United States Patent [19]

Herman et al.

[11] Patent Number: 5,744,353
[45] Date of Patent: Apr. 28, 1998

US005744353A

[54] CYTOLYTIC T CELL LINES WHICH BIND TO COMPLEXES OF TUMOR REJECTION ANTIGENS AND HLA-B44 MOLECULES

[75] Inventors: Jean Herman; Pierre Coulie; Thierry Boon-Falleur; Pierre van der Bruggen; Immanuel Luescher, all of Brussels, Belgium

[73] Assignee: Ludwig Institute for Cancer Research, New York, N.Y.

[21] Appl. No.: 796,883

[22] Filed: Feb. 6, 1997

Related U.S. Application Data

[60] Division of Ser. No. 602,506, Feb. 20, 1996, which is a continuation-in-part of Ser. No. 531,864, Sep. 21, 1995, which is a continuation-in-part of Ser. No. 373,636, Jan. 17, 1995, which is a continuation-in-part of Ser. No. 253,503, Jun. 3, 1994, Pat. No. 5,589,334.

[51] Int. Cl.$^6$ ........................................... C12N 5/06
[52] U.S. Cl. ........................................ 435/325; 435/372.3
[58] Field of Search ................... 435/328, 372.3, 435/325

[56] References Cited

U.S. PATENT DOCUMENTS 5,405,940 4/1995 Boon et al. ............................ 530/328

OTHER PUBLICATIONS

Tiercy et al. Human Immunology 41:207–15, 1994.
Salgaller et al. Cancer Immunol. Immunother. 39:105–116, Aug. 1994.
Fleischauer et al. Tissue Antigens 311–17, 1994.

*Primary Examiner*—Anthony C. Caputa
*Attorney, Agent, or Firm*—Felfe & Lynch

[57] ABSTRACT

Tumor rejection antigens presented by HLA-B44 molecules are described. These peptides are useful in diagnostic and therapeutic methodologies. The tumor rejection antigens are derived from MAGE tumor rejection antigen precursors.

3 Claims, 19 Drawing Sheets

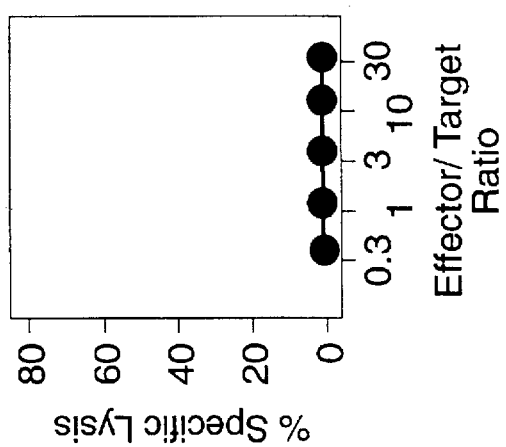
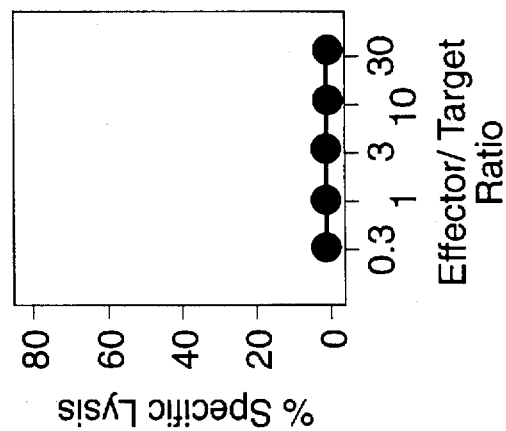
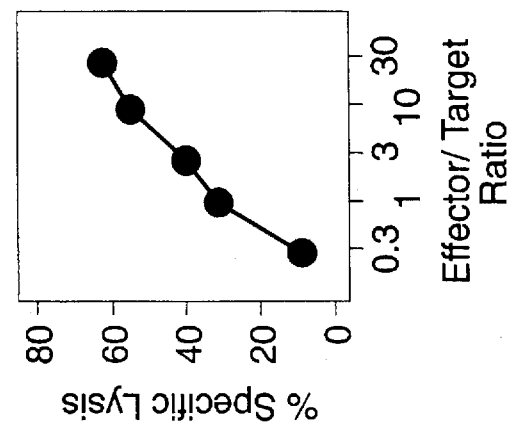

FIG. 8E

| Stimulator Cells | TNF Released by CTL (pg/ml) 20 40 60 80 100 |
|---|---|
| LB33-MEL.A-1 | ██████████████████ (~100) |
| A⁻B⁻D⁻ | ▪ |
| A⁻B⁻D⁻ + A28 | ▪ |
| A⁻B⁻D⁻ + B44 | ▪ |
| A⁻B⁻D⁻ + Cw7 | ▪ |

FIG. 8F

| Stimulator Cells | TNF Released by CTL (pg/ml) 20 40 60 80 100 |
|---|---|
| A⁻B⁻ | ▪ |
| A⁻B⁻ + A28 | ▪ |
| A⁻B⁻ + B44 | ▪ |
| A⁻B⁻ + Cw7 | ▪ |

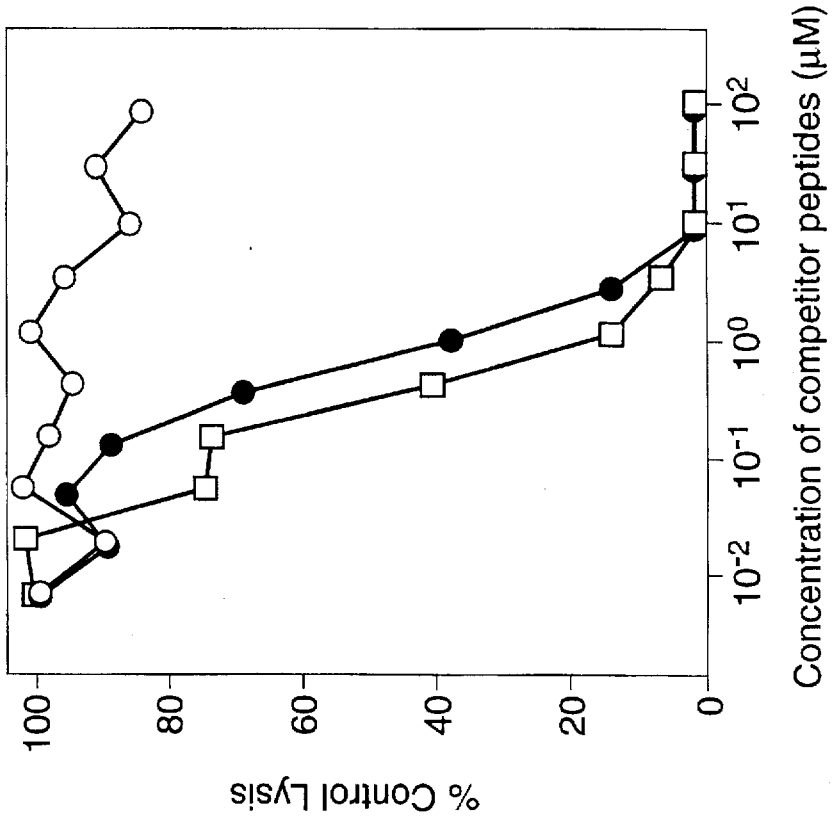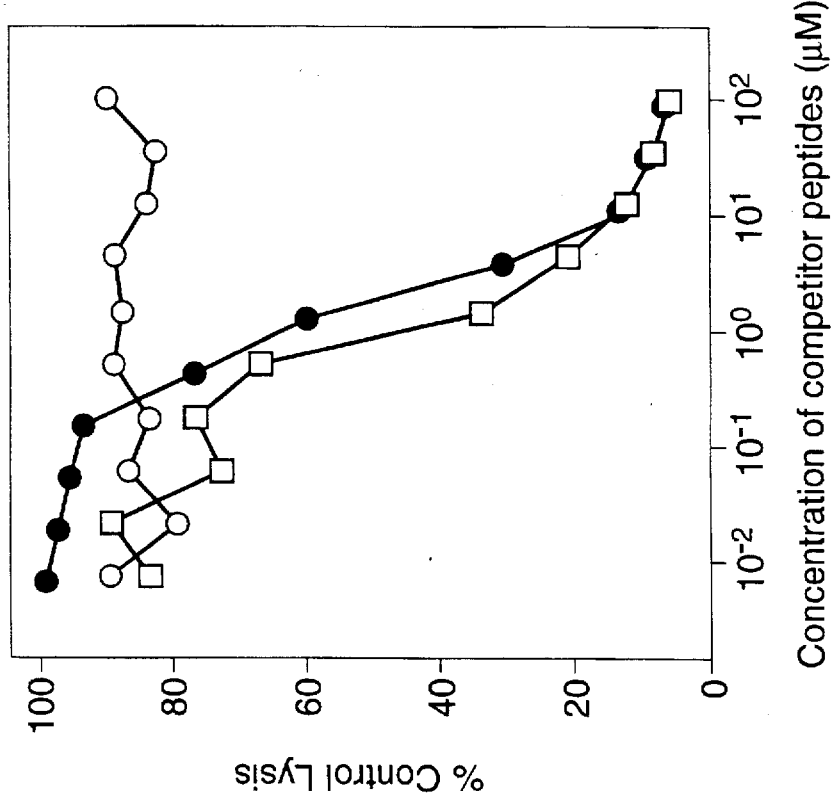

CYTOLYTIC T CELL LINES WHICH BIND TO COMPLEXES OF TUMOR REJECTION ANTIGENS AND HLA-B44 MOLECULES

RELATED APPLICATION

This application is a Divisional of Ser. No. 08/602,506 filed Feb. 20, 1996, which is a continuation-in-part of Ser. No. 08/531,864 filed Sep. 21, 1995, which is a continuation-in-part of Ser. No. 08/373,636, filed on Jan. 17, 1995, which is in turn a continuation-in-part of application Ser. No. 08/253,503 filed Jun. 3, 1994 now U.S. Pat. No. 5,589,334. All applications are incorporated by reference.

FIELD OF THE INVENTION

This invention relates to isolated peptides, derived from tumor rejection antigen precursors and presented by HLA molecules, HLA-B44 in particular, and uses thereof. In addition, it relates to the ability to identify those individuals diagnosed with conditions characterized by cellular abnormalities whose abnormal cells present complexes of these peptides and HLA molecules, the presented peptides, and the ramifications thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also see U.S. Pat. No. 5,342,774, incorporated by reference.

In U.S. Pat. No. 5,405,940, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBO J 7: 2715 (1988)). An early report of cDNA for the human enzyme is found in Kwon, U.S. Pat. No. 4,898,814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application Ser. No. 08/081,673 now U.S. Pat. No. 5,437,974, filed Jun. 23, 1993 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules. These are described in Ser. No. 08/203,054, now U.S. Pat. No. 5,530,096 filed Feb. 28, 1994 and incorporated by reference.

U.S. patent application Ser. No. 08/233,305 now U.S. Pat. No. 5,579,117 filed Apr. 26, 1994 and incorporated by reference, disclosed that tyrosinase is also processed to an antigen presented by HLA-B44 molecules. The finding was of importance, because not all individuals are HLA-A2$^+$. The fact that tyrosinase is processed to an HLA-B44 presented peptide, however, does not provide for a universal approach to diagnosis and treatment of all HLA-B44$^+$ tumors, because tyrosinase expression is not universal. Further, the fact that tyrosinase is expressed by normal cells as well as tumor cells may suggest some caution in the therapeutic area.

Population analysis indicates that about 22–24% of the caucasian population expresses the HLA-B44 molecule. See, e.g., Imanishi, et al., in Tsuji et al., ed., "HLA 1991, Vol. I, XI$^{th}$ International Histocompatibility Workshop And Conference", Oxford University Press, 1991; Lee in Lee, ed., The HLA System: A New Approach. Springer, pp. 141–178 (1990). Prior work has shown that about 76% of all metastatic melanoma tumors express MAGE-3 (Brasseur, et al., int. J. Cancer 63: 375–380 (1995)). Thus, approximately 17% of metastatic melanomas in the caucasian population should present complexes of HLA-B44 and MAGE-3 derived peptides on their surfaces, with clear implications for diagnosis and therapy. Five different HLA-B44 alleles have been identified, as can be seen via Fleischhauer, et al., Tissue Antigens 37: 133–137 (1991); Petersdorf, et al., Tissue Antigens 44: 211–216 (1994); Yao, et al., Immunogenetics 40: 310; Yao, et al., Human Immunol 42: 54–60 (1995); Yao, et al., Immunogenetics 41: 387 (1995). Among the caucasian population which expresses HLA-B44, 61% present the HLA-B*4402 allele, and 36% present allele HLA-B*4403. See Yao, et al., Human Immunol. 42: 54–60 (1995). There is a single difference between these two alleles which occurs at amino acid 156. In HLA-B*4402, this position is occupied by Asp, while it is occupied by Leu in HLA-B*4403. Bone marrow allograft rejections, and Graft versus Host disease have been observed between donors and recipients which differ with respect to the HLA-B*4402 and HLA-B*4403 alleles. Since amino acid 156 is located in the middle of an α2 helix and extends into the peptide binding site, it was of interest to determine if these different HLA-B44 alleles present different peptides.

Khanna, et al., J. Exp. Med. 176: 169–179 (July 1992), disclose an HLA-B44 binding peptide, which is discussed further infra. The Khanna peptide is not related to the peptides claimed herein.

Kita, et al., Hepatology 18(5): 1039–1044 (1993), teach a 20 amino acid peptide alleged to bind to HLA-B44 and to provoke lysis.

Thorpe, et al., Immunogenetics 40: 303–305 (1994), discuss alignment of two peptides found to bind to HLA-B44, and suggest a binding motif generally. The Thorpe disclosure speaks of a negatively charged amino acid at position 2, and one at position 9 which may be hydrophobic, or positively charged.

Fleischhauer, et al., Tissue Antigens 44: 311–317 (1994) contains a survey of HLA-B44 binding peptides.

It has now been found that the MAGE-3 tumor rejection antigen precursor is processed to a tumor rejection antigens presented by HLA-B44 molecules. It is of interest that this peptide differs from a peptide also derived from MAGE-3 and known to bind to HLA-A1, by a single, added amino acid at the N-terminus. This, inter alia, is the subject of the invention disclosure which follows.

BRIEF DESCRIPTION OF THE FIGURES

FIG. 1 shows the results of chromium release assays using each of three different cell lines (LB33-MELc1, LB33 EBV-B, and K562), by cytolytic T cell clone 159/5. The data are presented in terms of effector/target ratios vs % of lysis.

FIG. 8A–E show the production of tumor necrosis factor (TNF) by CTL clones stimulated by antigen loss variants, transfected with various HLA alleles. Untransfected LB33-MEL.A-1 cells were used as controls, as were antigen loss variants. The CTL clones used were 159/3, 159/5 and 204/26, 179 c/50, and 202/1 corresponding to anti-A, anti-B, an anti-Ca anti-Cb, and anti-D CTLs, respectively.

FIG. 10A depicts the lytic activity of anti-E CTL clone LB33-CTL-269/1 on autologous melanoma cells, while

FIG. 14 shows the results of studies wherein SEQ ID NOS: 17 and 3 were tested in competitive binding assays.

DETAILED DESCRIPTION OF PREFERRED EMBODIMENTS

EXAMPLE 1

Melanoma cell line LB33-MEL which has been available to researchers for many years, was used in the following experiments. A clone derived therefrom was also used. The clone is referred to hereafter as LB33-MELc1.

Samples containing mononuclear blood cells were taken from patient LB33. The melanoma cell line was contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39: 390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS (i.e., from fetal calf serum) and incubated for 45 minutes at 37° C. with 200 µCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% $CO_2$ atmosphere.

Plates were centrifuged again, and 100 ul aliquots of supernatant were collected and counted. Percentage of $^{51}$Cr release was calculated as follows:

$$\% \,^{51}Cr\;release = \frac{(ER-SR)}{(MR-SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

These experiments led to isolation of CTL clones LB33-CTL-159/5. FIG. 1 shows that this clone lysed tumor cells, but not EBV-B cells, or K562 cells.

Following the same protocol, a second CTL clone, i.e., LB33-CTL-159/3 was isolated. These lines will be referred to as "159/5" and "159/3", respectively. This second CTL has specificity differing from 159/5. This was ascertained following isolation of two antigen loss variants which (i) are lysed by 159/5 but not 159/3 and (ii) are not lysed by 159/5 and are lysed by 159/3. These variants are referred to as A$^-$ and B$^-$, respectively.

Figure 2:
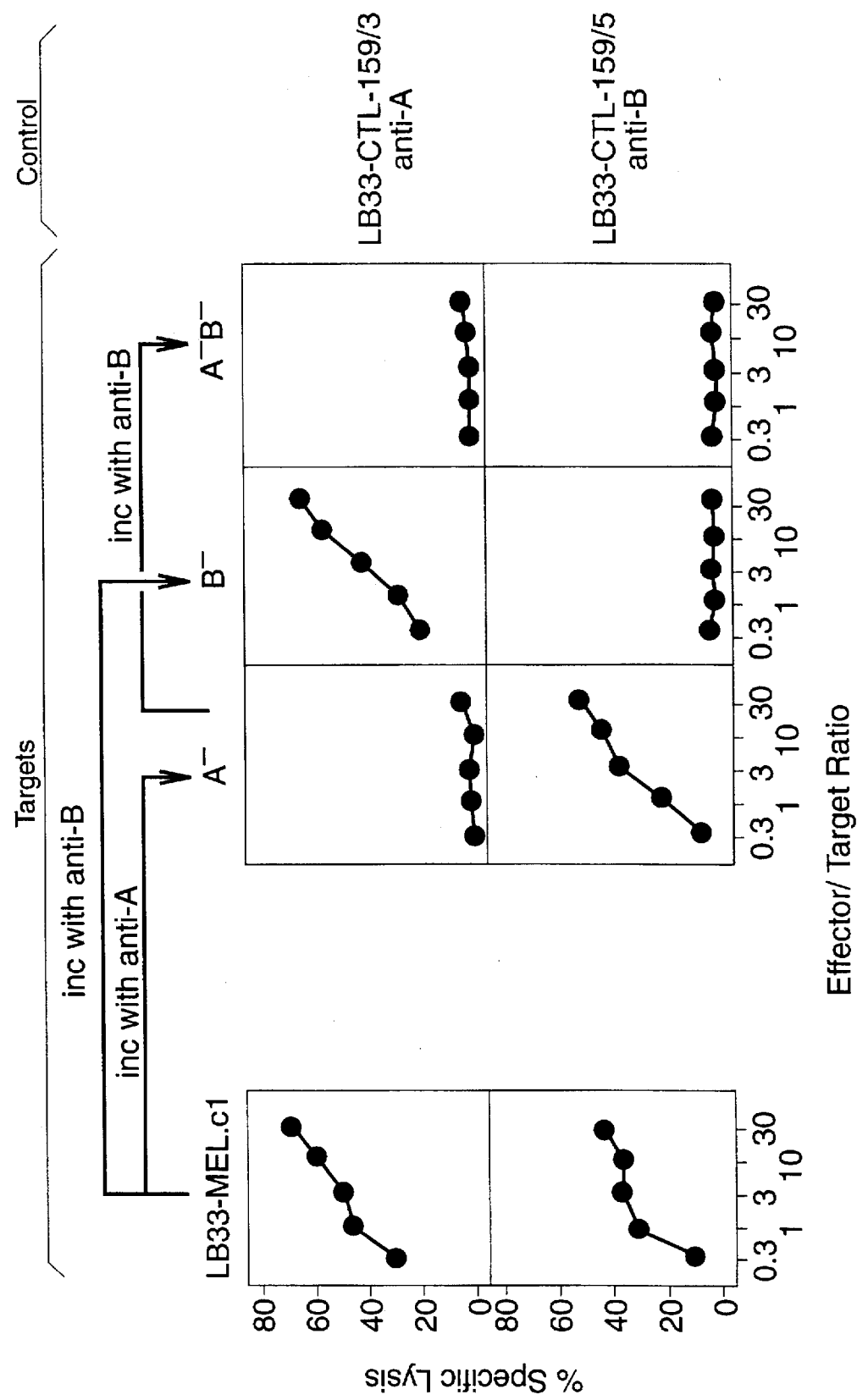
FIG. 2 shows the result of lysis studies which identified cell variants "A⁻", "B⁻", and "A⁻,B⁻". Again, a chromium release assay was used. Cell line LBB33-MELc1 is A⁺B⁺, as is indicated by the positive lysis with both CTL lines tested. CTL 159/93 is anti-A, while CTL 159/5 is anti-B.

The A$^-$ variant was then immunoselected with 159/5, and a third variant was obtained, which was not lysed by either 159/5 or 159/3. This variant is referred to as A$^-$B$^-$. FIG. 2 summarizes the results of the lysis assays, leading to isolation of the variants.

EXAMPLE 2

It was of interest to determine the pattern of HLA expression of variant A$^-$B$^-$. The patient from whom parent line LB33-MEL was derived was typed as HLA-A24, A28, B13, B44, Cw6, Cw7. When PCR expression analysis was carried out, it was found that both LB33-MELc1, and the B$^-$ variant express all six alleles; however, the A-B$^-$ variant does not express HLA-A28, B44, and Cw7. As a result, it was concluded that one of these HLA molecules presents the antigen leading to lysis by CTLs. The following example explores this further.

EXAMPLE 3

Figure 3:
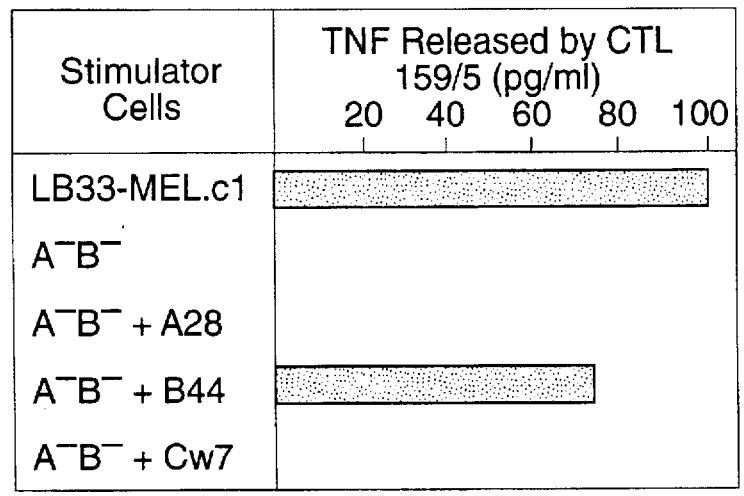
FIG. 3 shows results obtained when the variant A⁻B⁻ was transfected with coding sequences for each of HLA-A28, HLA-B44, and HLA-Cw7, as compared to a control line. The results are depicted in terms of the sensitive TNF release assay (pg/ml), where CTL 159/5 was used.

Samples of the A$^-$B$^-$ variant were transfected by plasmid pcDNA-I/AmpI which had cloned therein, one of HLA-A28, HLA-B44, or HLA-Cw7. Following selection, the cells were tested in a TNF release assay, following Traversari, et al., Immunogenetics 35: 145–152 (1992), incorporated by reference herein. The results are summarized in FIG. 3, which shows that HLA-B44 is clearly implicated in the presentation of the antigen.

EXAMPLE 4

Once the presenting HLA molecule was identified, studies were carried out to identify the molecule, referred to hereafter as the "tumor rejection antigen precursor" or "TRAP" molecule which was the source of the presented peptide.

To do this, total mRNA was isolated from cell line LB33-MELc1. The messenger RNA was isolated using an oligo-dT binding kit, following well recognized techniques. Once the messenger RNA was secured, it was transcribed into cDNA, again using standard methodologies. The cDNA was then ligated to EcoRI adaptors and cloned into the EcoRI site of plasmid pcDNA-I/Amp, in accordance with the manufacturer's instructions. The recombinant plasmids were then electrophorated into DH5α E. coli (electroporation conditions: 1 pulse at 25 µfarads, 2500 V).

The transfected bacteria were selected with ampicillin (50 µg/ml), and then divided into pools of 100 bacteria each. Each pool represented about 50 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

The amplified plasmids were then transfected into eukaryotic cells. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 30 µl/well of DMEM medium containing 10% Nu serum, 400 µg/ml DEAE-dextran, 100 µM chloroquine, and 100 ng of a plasmid containing cDNA for HLA-B44 from LB33. Following four hours of incubation at 37° C., the medium was removed, and replaced by 50 µl of PBS containing 10% DMSO. This medium was removed after two minutes and replaced by 200 µl of DMEM supplemented with 10% of FCS.

Following this change in medium, COS cells were incubated for 48 hours at 37° C. Medium was then discarded, and 2000 cells of 159/5 were added, in 100 µl of Iscove's medium containing 10% pooled human serum and 25 U/ml IL-2. Supernatant was removed after 24 hours, and TNF content was determined in an assay on WEHI cells, as described by Traversari et al., Immunogenetics 35: 145–152 (1992), the disclosure of which is incorporated by reference. One pool stimulated TNF release above background, and these bacteria were cloned, and used in the following experiment.

EXAMPLE 5

Figure 4A:
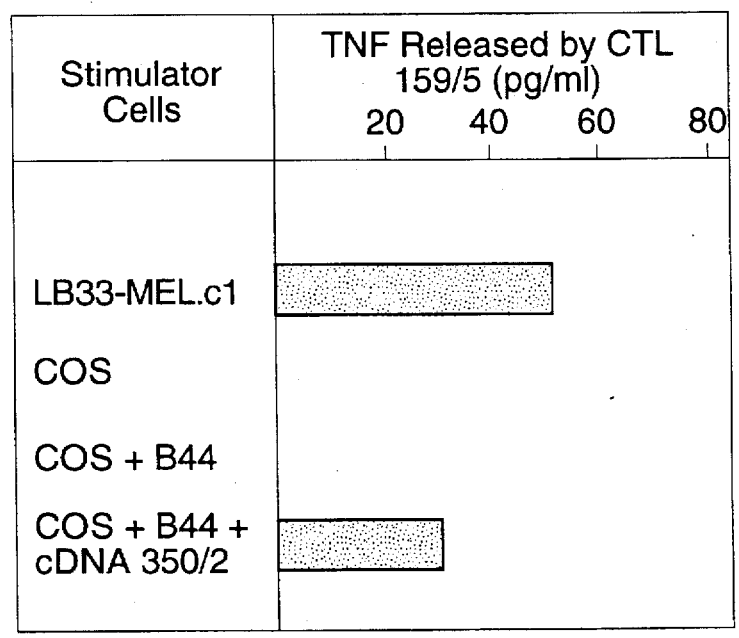
FIG. 4 (see panels A and B) shows TNF release by CTL 159/5, where COS cells were transfected with HLA-B44, or HLA-B44 plus a nucleic acid molecule in accordance with this invention.

Plasmid DNA was extracted from the bacteria cloned in Example 4, transfected into a new sample of COS cells in the same manner as described suora, and the cells were again tested for stimulation of 159/5. A positive clone was found in clone 350/2, as demonstrated by data summarized in FIG. 4A.

Figure 4B:
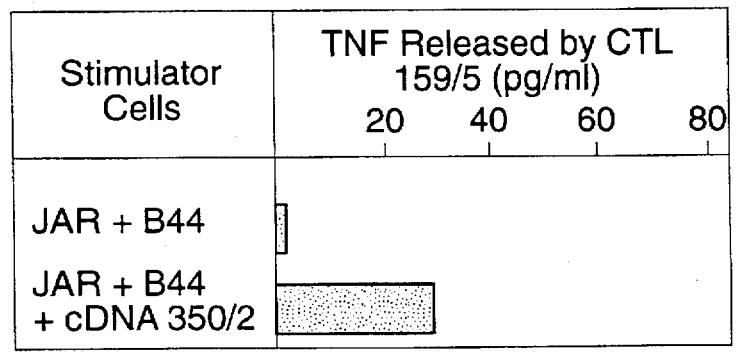
Figure 5A:
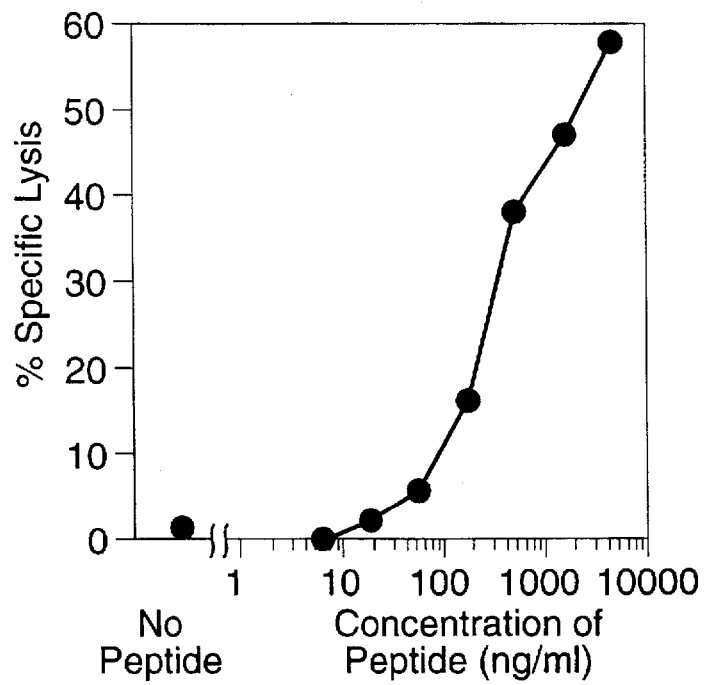
FIG. 5A depicts $^{51}$Cr release in EBV-B cells, when contacted with CTL 159/5.
Figure 5B:
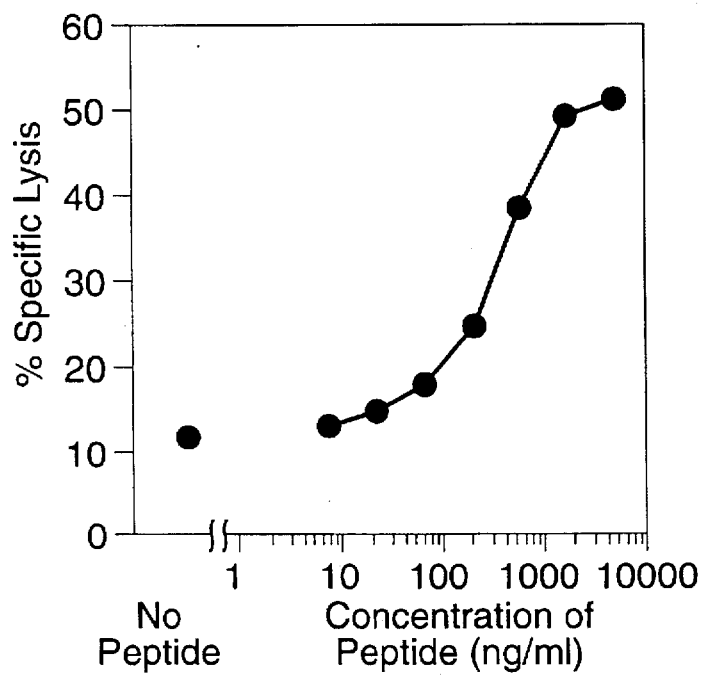
FIG. 5B is similar, but uses LB33-MEL B⁻ cells. In each of FIGS. 5A and 5B, the antigenic peptide of the invention was contacted to the cells prior to contact with the CTLs.

In order to confirm the results obtained to this point, the human choriocarcinoma cell line JAR, which is readily available from the American Type Culture Collection, was used. This cell line does not express HLA molecules, nor is it recognized by CTL 159/5. When JAR was transfected with HLA-B44 cDNA, it was still not recognized by CTL 159/5. Co-transfection with HLA-B44 and 350/2 cDNA, however, led to lysis, as is seen in FIG. 4B.

The plasmid from the positive clone was removed, and sequenced following art known techniques. Information shows that the plasmid insert was 1896 base pairs long, and showed no homology with any sequences in data banks. The nucleotide sequence is set forth herein as SEQ ID NO: 1.

EXAMPLE 6

Figure 6:
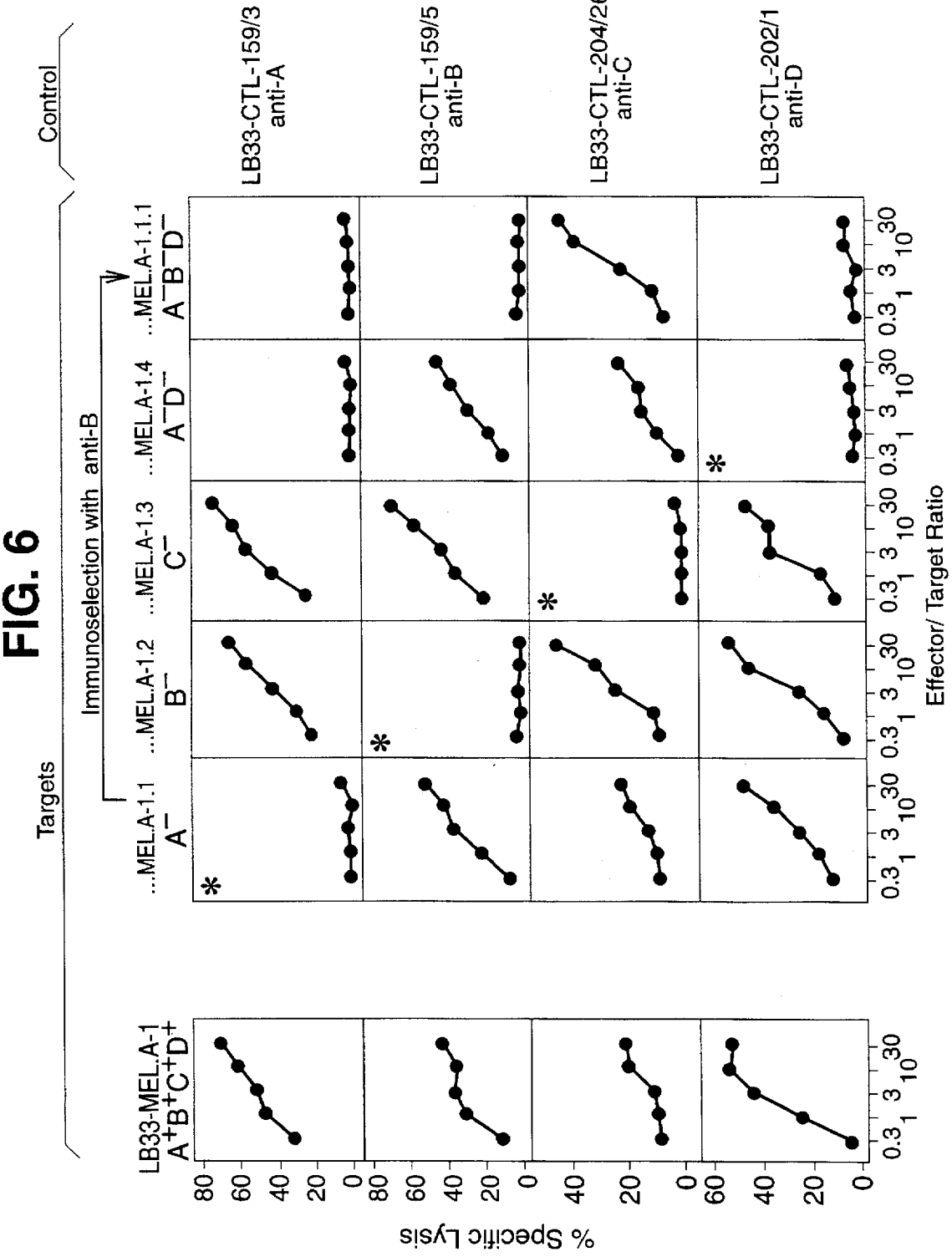
FIG. 6 shows the lytic activity of various autologous CTL clones on antigen loss variants derived from melanoma clonal line LB33.MEL.A-1.

In order to ascertain the peptide which was the tumor rejection antigen, fragments of SEQ ID NO: 1, averaging about 300 base pairs, were amplified via PCR, cloned into pcDNA-I/Amp, and then cotransfected into COS cells with plasmids encoding HLA-B44, following the protocols of the preceding examples. These experiments led to identification of the region corresponding to amino acid residues 683–955 of SEQ ID NO: 1 as encoding the antigenic peptide. This region was compared to the peptide described by Khanna, et al., J. Exp. Med. 176: 169–176 (7/92), and the peptide described in Ser. No. 08/233,305, filed Apr. 26, 1994, i.e.:

Glu Glu Lys Leu Ile Val Val Leu Phe (SEQ ID NO: 2)

corresponds to these residues. As such, a peptide corresponding to this sequence was synthesized, and used to sensitize HLA-B44$^+$ cell lines. The results are shown in FIGS. 6A and 6B, which depict the results of a $^{51}$Cr release assay using EBV transformed B cells (FIG. 6A), and the B$^-$ variant described supra (FIG. 6B). The cells were incubated with varying concentrations of the peptide for 30 minutes at 37° C., before adding CTL 159/5 (effector/target ratio: 10:1). Half maximal lysis was obtained with 100–200 ng/m of peptide.

EXAMPLE 7

Examples 1–6, set forth supra, describe work using the cell line LB33-Melc1. Additional cell lines were also derived from a cutaneous metastasis from patient LB33. One such line is LB33-MEL.A-1 which is used in the example which follows.

First, the cell line was used, in the same manner that the cell line of examples 1–6 was used (Herin et al., supra). Blood mononuclear cells (10$^6$/well), were stimulated with irradiated tumor cells (3/10$^5$ cells/well), in 2 ml of Iscove's medium, supplemented with 10% pooled human serum, asparagine-glutamine-arginine (36 mg/ml, 216 mg/ml, 116 mg/ml, respectively), 2-mercaptoethanol (0.05 mM), and 5 U/ml of human IL-4. IL-2 (10 U/ml) was added on the third day of cultivation. Sensitivity of the tumor cells to autologous CTLs was determined as in example 1, supra. The experiment yielded 82 stable cytolytic T lymphocytes, derived from seven independent cultures. All of these CTLs were CD8$^+$. They were specific for tumor cells in that they lysed LB33-MEL.A-1 cells, but not K562, or autologous, EBV transformed cells.

EXAMPLE 8

The fact that LB33-MEL.A-1 cells were lysed by autologous CTLs suggested the next experiment, which was to identify the antigens recognized by establishing antigen loss variants.

To do this, samples of the cell line were selected, four times, with the autologous CTL clone LB33-CTL 159/3, described supra. Each round of selection involved incubating, for 2–6 hours, 2–3×10$^7$ adherent tumor cells with a similar number of CTLs, in the same manner described supra. In each round, CTLs were washed away following the incubation, and the surviving adherent tumor cells were amplified prior to the next round of selection.

This procedure resulted in a clone resistant to CTL 159/3; however, when tested with additional autologous CTLs, it was found that CTL 159/5, described supra, did lyse the loss variant, as did additional CTL clones, including 204/26, and 202/1. Please see FIG. 6, the column labelled "MEL.A-1". Similarly, additional cell lines were established which were not lysed by one of these four CTL clones, but was lysed by the others. Note FIG. 6. Thus, at least four different antigens were found to be presented on the surface of LB33-MEL.A-1, because four distinct antigen-loss variants were identified. As set forth in FIG. 6, then, LB33-MEL.A-1 is considered "A$^+$B$^+$C$^+$D$^+$" for antigen expression (lysed by all of CTL 159/3, 159/5, 204/26, and 202/1); MEL.A-1.1 is A$^-$B$^+$C$^+$D$^+$ (not lysed by 159/3, lysed by others); MEL.A-1.2 is A$^+$B$^+$C$^+$D$^+$ (not lysed by 159/5; lysed by others), MEL.A-1.3 is A$^+$B$^+$C$^+$D$^+$ (not lysed by 204/26; lysed by others), and MEL.A-1.4 is A$^-$B$^+$C$^+$D$^-$ (not lysed by 202/1 or 159/3). Further, cell line MEL.A-1.1.1 was isolated, which was A$^-$B$^-$C$^+$D$^-$ (lysed only by 204/26).

When the 82 CTLs identified via example 7 were tested on these lines, 29 anti-A, 29 anti-B, 10 anti-C, and 14 anti-D clones were identified, suggesting that there were no other antigens being presented.

Selection with anti-D CTL clone 202/1 led to identification of a line which was also resistant to the anti-A CTL clone (159/3), as did selection with anti-B CTL (i.e., the resulting A$^-$B$^-$C$^+$D$^-$ line). This result suggests that A$^-$D$^-$ and A$^-$B$^-$D$^-$ antigen loss variants were actually HLA loss variants, with antigens A, B and D sharing the same HLA presenting molecule, or that different class I molecules had been lost together with the antigen loss variants. The following experiments pursued this issue.

EXAMPLE 9

The patient from whom the LB33 cell lines had been developed had been serologically typed, previously, as HLA-A24, A28, B13, B44, Cw6, Cw7. Studies were then carried out to determine the expression of HLA class I genes by the cell lines.

Semi-quantitative conditions for DNA amplification by PCR were established in order to assess the expression of each of the six class I alleles by the different LB33-MEL tumor cell clones. The Amplification Refractory Mutation System (ARMS) PCR methodology proposed by Browning et al, that relies on the perfect nucleotide matched needed at the 3' end of primers to ensure specificity of DNA amplifications was used. See Browning et al, Proc. Natl. Acad. Sci. USA 90: 2842 (1993) incorporated by reference herein. On the basis of sequences obtained in typing LB33, allele-specific primers that enabled discrimination of each one of the six alleles from the five others (5' primer followed by 3' primer) were synthesized.

A24: 5'-GCCGGAGTATTGGGACGA and 5'-GGCCGCCTCCCATTGC, (SEQ ID NO: 5 and 6)
A28: 5'-CCAGTATTGGGACCGGAAG and 5'-GGCCGCCTCCCACTTGT, (SEQ ID NO: 7 and 8)
B13: 5'-CGCCACGAGTCCGAGGAT and 5'-CCTTCCCGTCGTAGGCTA, (SEQ ID NO: 9 and 10)

B44: 5'-CGCCACGAGTCCGAGGAA and 5'-CCTTGCCGTCGTAGGCGT, (SEQ ID NO: 11 and 12)

Cw6: 5'-CCGAGTGAACCTGCGGAAA and 5'-GGTCGCAGCCATACATCCA (SEQ ID NO: 13 and 14)

Cw7: 5'-TACAAGCGCCAGGCACAGG and 5'-CTCCAGGTACGCTCTGTC (SEQ ID NO: 15 and 16)

To carry out semi-quantitative measurements of expression, 27 cycles of PCR amplification of reverse transcribed RNA were carried out with each set of primers, and DNA amplification was found to be in the linear range. The quantity of the amplified DNA was visually assessed with agarose gels stained with ethidium bromide. These quantities were compared to those obtained with a standard curve containing the products of RT-PCR amplification of serial dilutions of RNA from LBBB-MEL.A-1 cells. The expression of samples was normalized for RNA integrity by taking into account the expression level of the β-actin gene. The results were expressed relative to the level of expression by LB33-MEL.A-1 cells. The results of this work are set forth in Table 1, which follows. A "+++" indicates expression corresponding to more than half that of the LB33-MEL.A-1 cells, "++" means that expression was between ⅛ and ½ of that of LB33-MEL.A-1, a "+" means that expression was less than 1/8 of that of LB33-MEL.A-1 expressed and "−" means there was no expression.

TABLE 1

Expression of HLA class I by the antigen-loss variants derived from LB33-MEL.A cells.

| | LB33-MEL.A-1 tumor cells | | | | | |
|---|---|---|---|---|---|---|
| Expression | | Antigen-loss variants | | | | |
| of | LB33-MEL.A-1 | A⁻ | B⁻ | C⁻ | A⁻D⁻ | A⁻B⁻D⁻ |
| A. | Gene expression | | | | | |
| A24 | +++ | +++ | +++ | − | ++ | +++ |
| A28 | +++ | +++ | +++ | +++ | + | − |
| B13 | +++ | +++ | +++ | + | +++ | +++ |
| B44 | +++ | +++ | +++ | +++ | ++ | − |
| Cw6 | +++ | +++ | +++ | + | +++ | +++ |
| Cw7 | +++ | ++ | +++ | +++ | + | − |

As seen, both MEL.A-1 cells, and B⁻ variant expressed similar levels of all six HLA alleles. The A⁻ variant showed an approximately 4-fold decrease in expression of Cw7. The remaining antigen loss variants showed decreases in expression of sets of three alleles. For C⁻ cells, reduced levels of expression for HLA-A24, B13, and Cw6 were found, while A⁻D⁻, and A⁻B⁻D⁻ variants showed reduction in A28, B44, and Cw7 expression. This suggests that A24-B13-Cw6, and A28-B44-Cw7 constitute two HLA class I haplotypes of patient LB33, and that reduced expression of these haplotype probably accounted for loss of antigen expression by the immunoselected tumor cells.

EXAMPLE 10

The next experiments were designed to confirm a correlation between HLA gene expression, and lysis by CTLs. To do this, the expression of a given HLA gene, as determined supra, was compared with the results obtained using a standard antibody assay. Only A24, A28 and B13 were tested, using murine antibodies specific thereto (C7709A1 for A24; 2.28M1 for A28, and TÜ 48 for B13). Binding of antibody was determined by incubation with antibody, washing and then contacting with goat anti-mouse Ig antibodies, coupled to fluorescein. The cells were then analyzed by flow cytometry, a standard technique.

Figure 7:
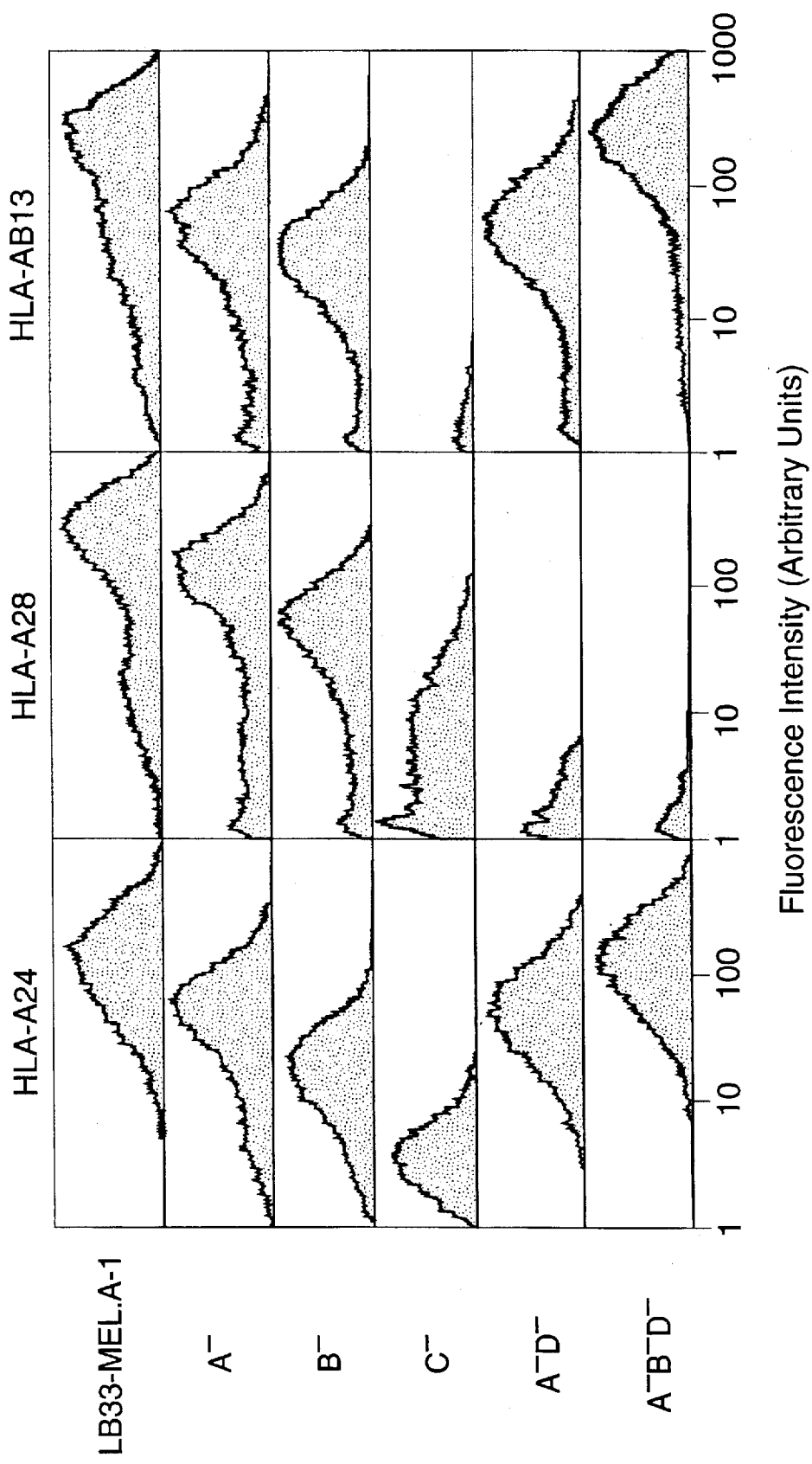
FIG. 7 presents results showing expression of HLA-A24, A28 and B13 molecules by antigen loss variants of LB33-MEL.A-1. Tumor cells had been incubated with mouse antibodies against particular HLA molecules, and were then labeled with fluorescein tagged goat anti-mouse antibodies.
Figure 8A:
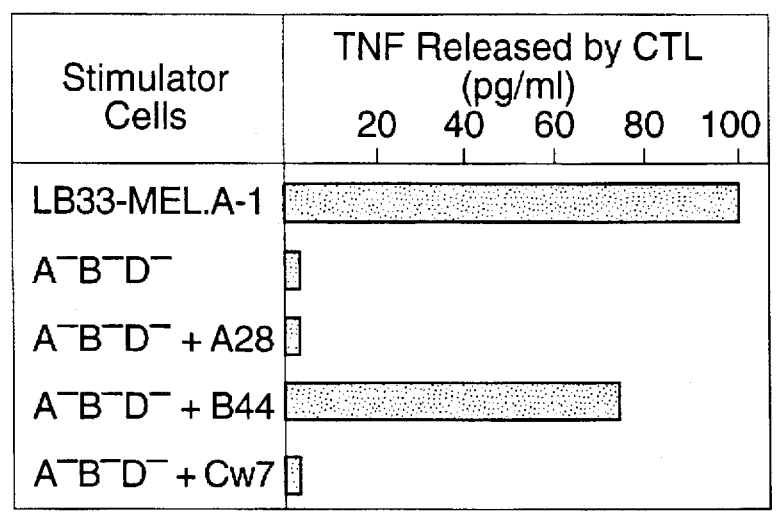
Figure 8B:
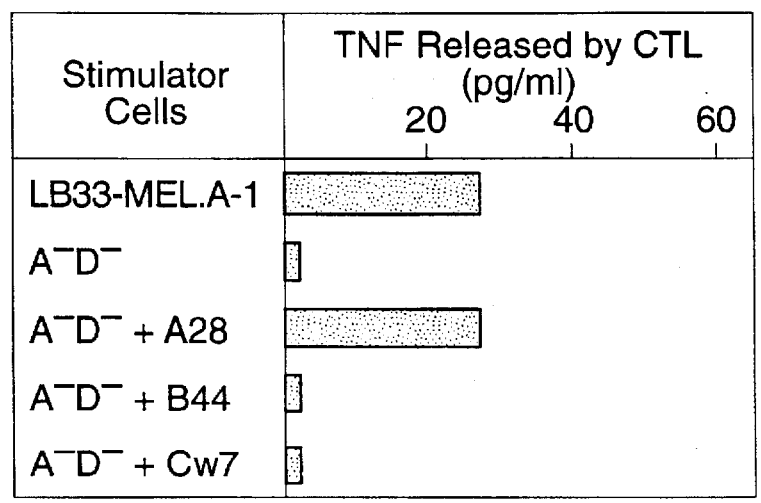
Figure 8C:
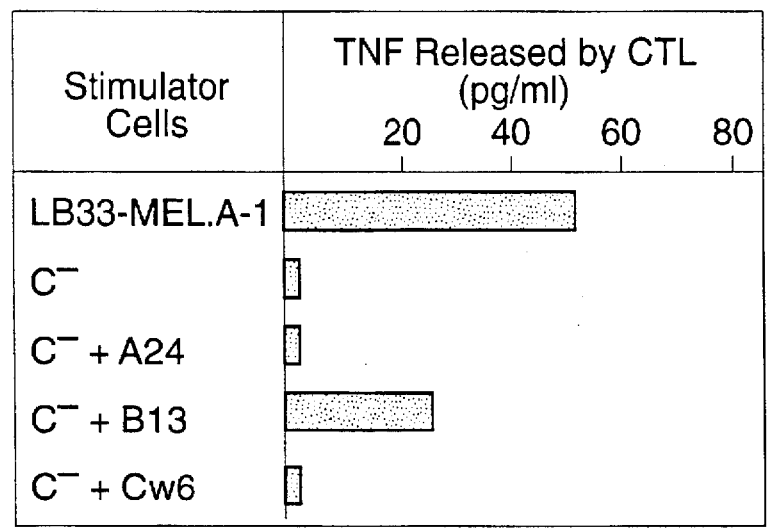
Figure 8D:
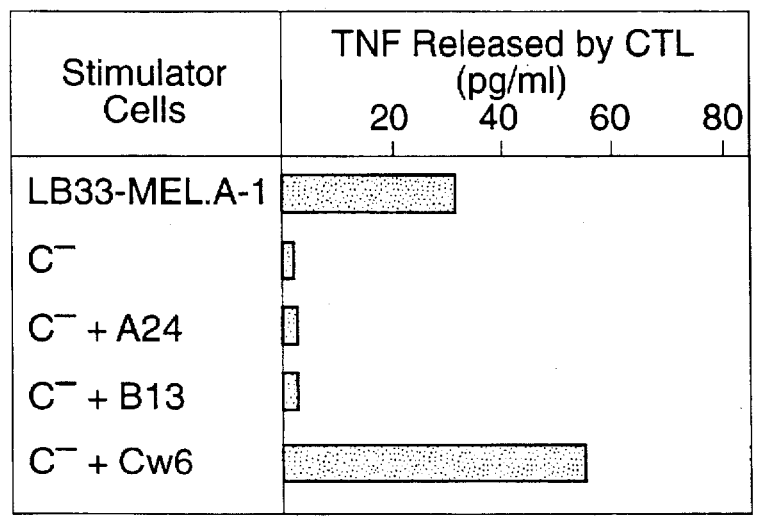
Figure 9:
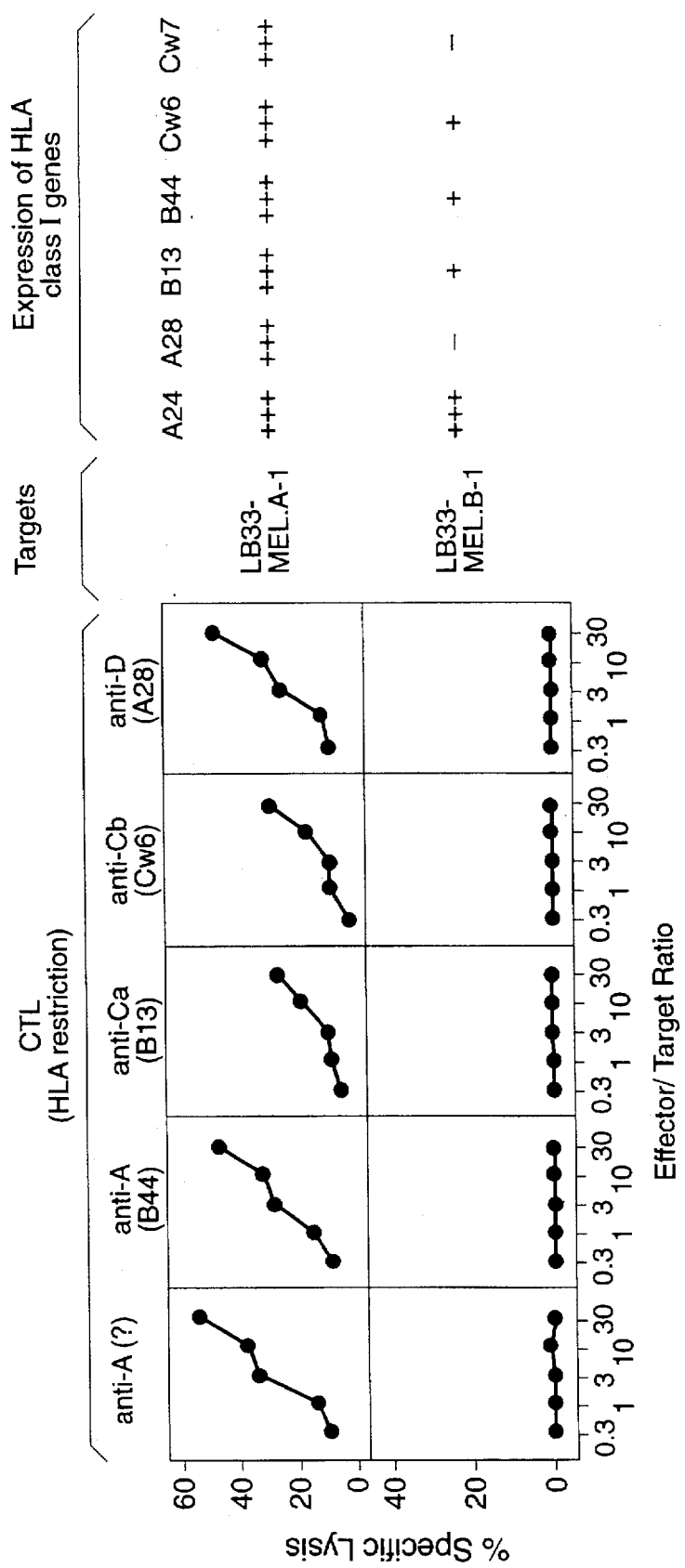
FIG. 9 sets forth further data regarding the cytolytic activity of the CTL clones described in FIGS. 6 and 8. The cell line LB33-MEL.A had been obtained following surgery in 1988. Cell line LB33-MEL.B was obtained from a metastasis which developed in the patient in 1993.

Table 2 summarizes the results, which are also shown in FIG. 7. In table 2 that follows, the indicated level of HLA expression corresponds to the mean intensity of fluorescence shown in FIG. 6. Values are expressed relative to levels found in LB33-MEL.A-1 cells.

It appears from these results that when levels of HLA expression estimated to range below ⅛ of that of LB33-MEL.A-1 cells, undetectable or barely detectable levels of HLA surface molecules are found, thus suggesting that antigen presentation to CTL was unlikely for the given HLA molecule.

In view of this, and assuming that C⁻, A⁻D⁻ and A⁻B⁻D⁻ selected cells had lost expression of antigen because of lack of HLA molecules, it appeared to be the case that the class I presenting molecules for antigen A were A28 or Cw7, B44 for antigen B, A24 or B13 or Cw6 for antigen C, and A28 or Cw7 for antigen D.

TABLE 2

| | | Antigen-loss variants | | | | |
|---|---|---|---|---|---|---|
| Expression of | LB33-MEL.A-1 | A⁻ | B⁻ | C⁻ | A⁻D⁻ | A⁻B⁻D⁻ |
| | Expression of surface antigen | | | | | |
| A24 | 100 | 33 | 13 | 4 | 41 | 95 |
| A28 | 100 | 29 | 14 | 3 | 1 | 1 |
| B13 | 100 | 27 | 22 | 1 | 40 | 230 |

EXAMPLE 11

The experiments detailed above were followed by additional work to determine, definitively, the presenting molecules for the antigens expressed by the LB33-MEL.A cells. To do this, tumor cells which had lost expression of particular HLA class I molecules were transfected, using the classic calcium phosphate precipitation method, with expression vector pcDNA3, into which the particular class I cDNA was cloned. This vector contains the neo^R marker. Transfectants were selected with 1.5 mg/ml of G418, and were then used to stimulate CTL clones, using the TNF assay set forth in the previous examples.

FIG. 8 depicts these results. Expression of antigen B was restored in A⁻B⁻D⁻ cells by transfection with a plasmid carrying HLA-B44, but not with plasmids containing HLA-A28 or HLA-Cw7. The expression of antigen C was restored in C⁻ cells by transfection with HLA B13. Four other anti-C CTL clones also recognized C⁻ cells, but five other anti-C CTL clones, including depicted CTL 179C/50, did not; rather, these CTLs recognized C⁻ cells transfected with HLA-Cw6. Thus, it may be concluded that there are two groups of anti-C CTL clones. One recognizes an antigen presented by HLA-B13, and the other an antigen presented by HLA-Cw6. As for antigen D, A⁻D⁻ cells were restored to A⁻D⁺ via transfection with HLA-A28. None of the cDNA restored expression of antigen A (i.e., tested HLA A28, B44, Cw7), although it clearly is presented by HLA-class I molecules, because lysis by anti-A CTLs is completely inhibited by anti-class I monoclonal antibody W6/32. It is possible that this antigen may be presented by a non-A, B, C class I molecule, of which two alleles were present in patient LB33, one of these being lost, together with the A28-B44-Cw7 haplotype in A⁻D⁻/A⁻B⁻D⁻ cells.

The results for antigen C have led to a change in nomenclature. There are two antigens referred to as antigen, Ca and antigen Cb, hereafter.

EXAMPLE 12

In further experiments, the question of whether or not cells of the line LB33-MEL.B could be recognized by autologous cell lines, was addressed.

Irradiated LB33-MEL.B.1 cells were used in the same manner as was used, supra (Herin, et al), to stimulate autologous lymphocytes. The lymphocytes had been taken from patient LB33 in 1990 or 1994.

Only the lymphocytes from 1994 lysed LB33-MEL.B-1 cells; however, they did not lyse LB33-MEL.A cells. Thus, the LB33-MEL.B-1 line presents an antigen not found on LB33-MEL.A.

Figure 10A:
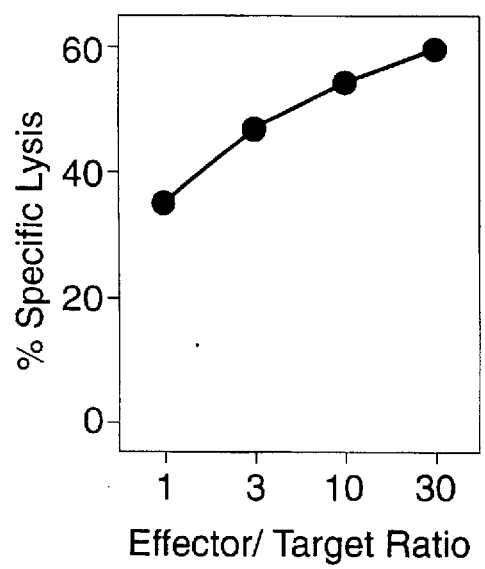

The experiments described herein parallel those described supra and, as in the prior experiments, another panel of CD8$^+$ CTL clones were established. The panel of reactivity of CTL 269/1 is shown in FIG. 10A. Note reaction with "MEL.B-1", but not "MEL.A-1". The new antigen defined thereby is referred to as LB33-E.

Figure 10B:
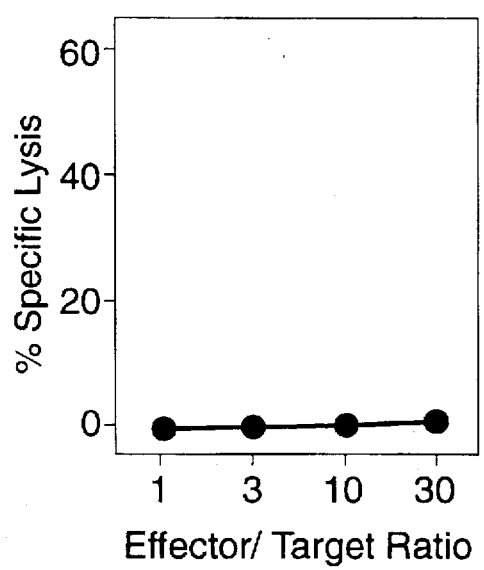
FIG. 10B shows production of TNF by the same CTL clone, following stimulation by LB33-MEL.B-1 cells. The stimulator cells (10,000/microwell) had been incubated for 16 hours with 3000 CTLs. The concentration of TNF released by the CTLs had been measured using TNF sensitive WEHI-164c13 cells. Anti HLA-A24 monoclonal antibody C7709A2 was used to inhibit CTL stimulation, by adding a 1/100 dilution of ascites fluid obtained from mice inoculated with the hybridoma cells.
Figure 10C:
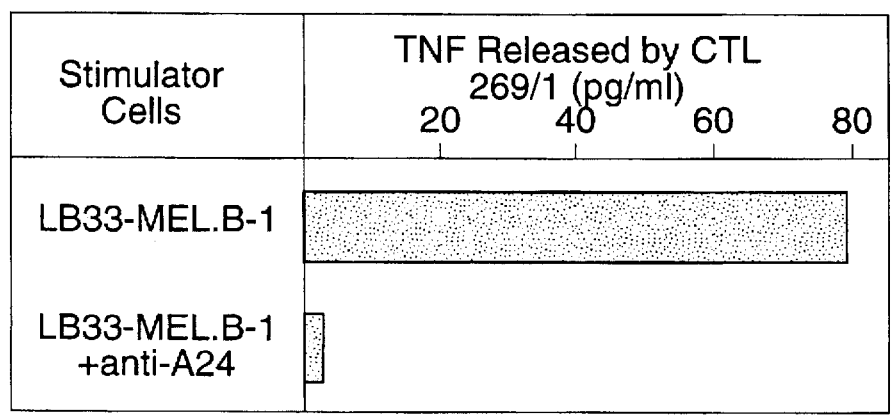

In antibody inhibitory experiments, mAbs to HLA-A24 inhibited lysis. This is shown in FIG. 10B. Hence, the "E" antigen is presented by HLA-A24.

EXAMPLE 13

Fleischhauer et al., Tissue Antigens 44: 311–317 (1994), incorporated by reference, teach a consensus motif for HLA-B44 binding. This motif is described as a nine or ten amino acid polypeptide, where Glu predominates at second position, Tyr or Phe is present at the last position (position 9 or 10), and hydrophobic residues, such as Met, are at the third position.

The MAGE-3 TRAP amino acid sequence contains a stretch of amino acids at position 167–176, which corresponds to this motif. The amino acid sequence is:

Met Glu Val Asp Pro Ile Gly His Leu Tyr (SEQ ID NO: 17).

The HLA-B44 motif is known to contain at least two major subtypes, referred to as HLA-B* 4402 and HLA-B* 4403. The MHC molecule appears on 23% of all caucasians. When this figure is combined with standard analyses of melanoma, it is concluded that 15% of caucasian melanoma patients should present HLA-B44 on the surface of their melanoma cells. Thus, it was of great interest to determine if the peptide of SEQ ID NO: 17 or related molecules can in fact be used to identify HLA-B44 cells, and to provoke their lysis following binding to the MHC molecule. As noted in prior examples, the peptide of SEQ ID NO: 2 was shown to bind to HLA-B44 positive cells. A peptide was designed which was similar to SEQ ID NO: 2, except for having Ala at position 8, rather than Leu. This new peptide, i.e.:

Glu Glu Lys Leu Ile Val Val Ala Phe (SEQ ID NO: 18), was tested in a competition assay with SEQ ID NO: 2. This peptide was used in view of result obtained in experiments not reported here. Briefly, derivatives of SEQ ID NO: 2 were prepared, wherein each derivative contained an Ala at a position not occupied by Ala in SEQ ID NO: 2. CTL clone 159/5 was slightly better at recognizing complexes containing SEQ ID NO: 18 than SEQ ID NO: 2, making it an excellent reagent for competitive assays. Competition was carried out using C1R cells, described by Storkus et al., J. Immunol 138: 1657–1659 (1987). These C1R cells are MHC class I negative, lymphoblastoid cells. The C1R cells were transfected with a cDNA for HLA-B*4402, or with genomic DNA for HLA-B*4403, using the same methodology given supra. The cDNA for HLA-B*4402 is set forth by Fleischhauer, et al, Tissue Antigens 44: 311–317 (1994), while the genomic DNA for HLA-B*4403 is given by Fleischhauer, et al. (1990) New Eng. J. Med 323: 1818–1822 (1990). Both papers are incorporated by reference.

The cells were labelled with $^{51}$Cr for one hour at 37° C., in the presence of anti-HLA class I monoclonal antibody W6/32 (30% (v/v) of culture medium of the hybridoma cells). This increases the ability of the cells to present antigenic peptides to T cells.

Labelled cells were washed, and incubated for 30 minutes at 20° C., in serum free medium, together with various concentrations of competitor peptides. These peptides included:

Ser Glu Ile Trp Arg Asp Ile Asp Phe (SEQ ID NO: 3) which binds to HLA-B44 molecules, as discussed, supra Phe Leu Arg Gly Arg Ala Tyr Gly Leu (SEQ ID NO: 19), which is encoded by EBV gene EBNA-3A and binds to HLA-B8 (Burrows, J. Exp Med 171: 345–349 (1990)), and SEQ ID NO: 17.

Figure 11A:
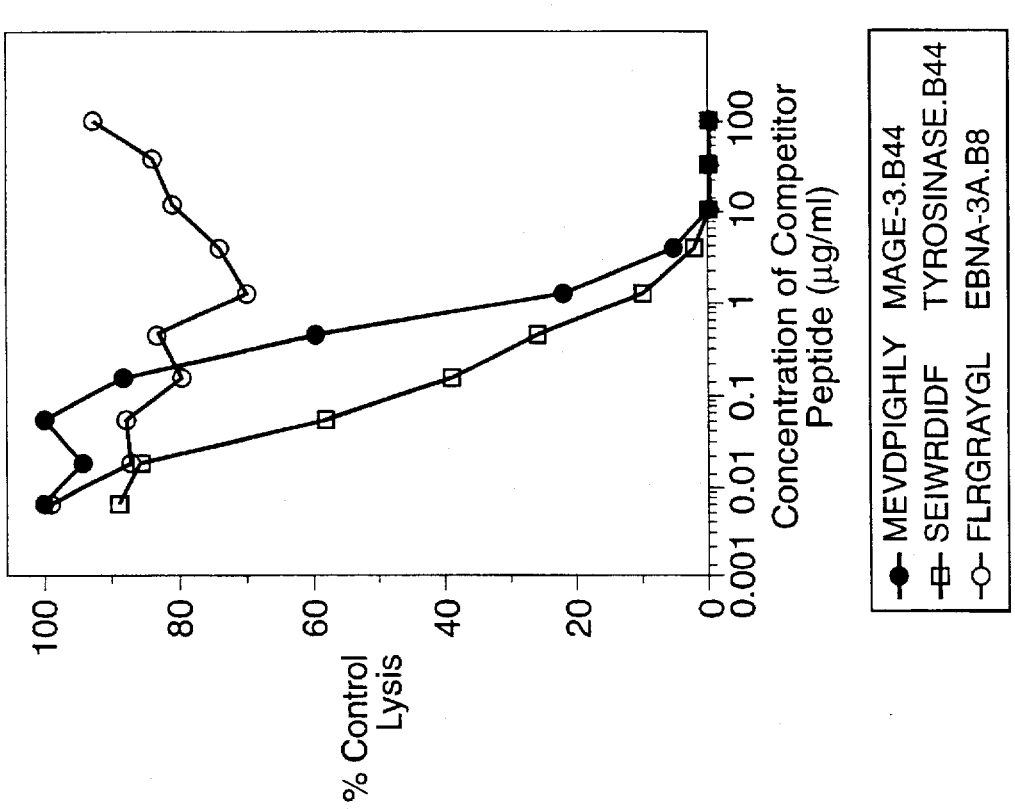
FIGS. 11A and 11B show the results of assays, wherein SEQ ID NOS: 17, 18, 19 and 3 were tested in competitive binding assays.
Figure 11B:
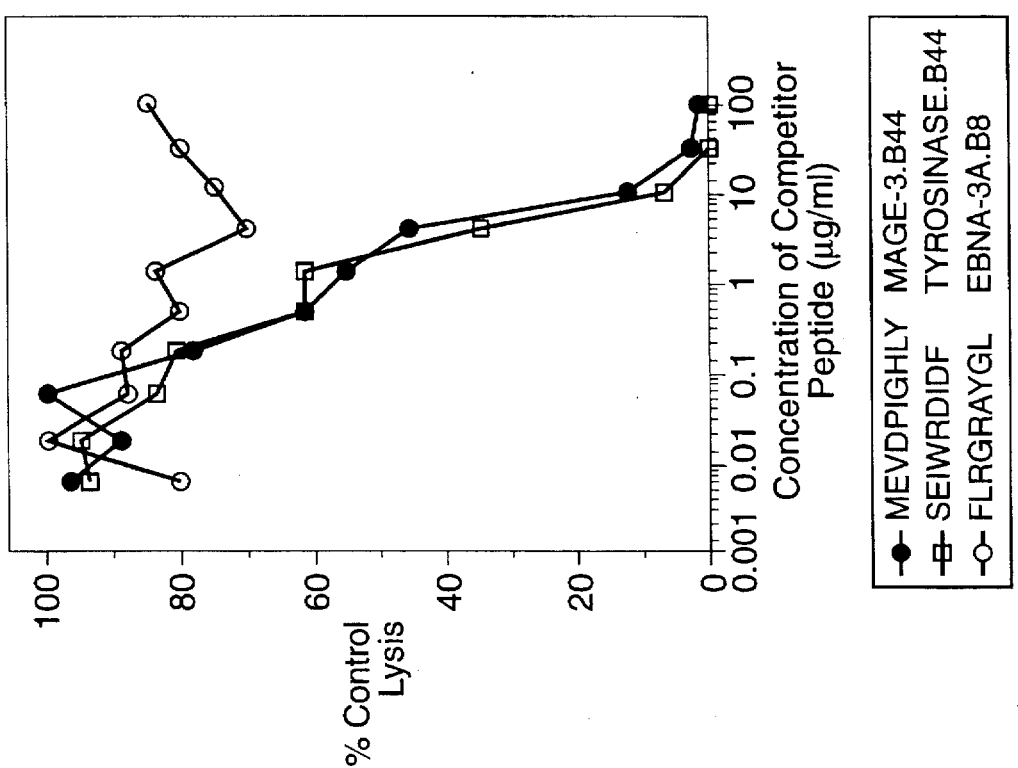

The peptide of SEQ ID NO: 18 was then added in the serum free culture medium at a final concentration of 45 ng/ml, (C1R-B4402$^+$ cells), or 160 ng/ml (C1R-B4403$^+$ cells). The cells were incubated for 30 minutes at 20° C., and washed twice in Iscove's medium plus 2% fetal calf serum. The CTL clone LB33-CTL 159/5 was added in Iscove's medium and 10% human serum, at an E:T ratio of 20. The release of $^{51}$Cr was measured after three hours, and is shown in FIGS. 11A and 11B, for C1R-B*4402 and C1R-B*4403 cells. The data presented in FIG. 11, show clear evidence of competition.

EXAMPLE 14

Additional experiments were then carried out following those described in Example 13.

Cytolytic T cell clones (CTLs) were derived from two subjects, referred to as LB 816 and LB 822, respectively. These subjects showed no evidence of cancer.

Blood mononuclear cells (BMCs) were isolated from the subjects, using density gradient centrifugation. T lymphocytes in the BMCs were purified by rosetting, using sheep red blood cells which had been treated with aminoethylisothiouronium bromide, and then labelled with an anti-CD8 monoclonal antibody coupled to magnetic microbeads. The CD8$^+$ cells were sorted by passage through a magnetized area, and then stored at $-80°$ C. in Iscove's culture medium, supplemented with 10% human serum, 116 mg/l L-arginine, 36 mg/l L-asparagine, and 216 mg/l of L-glutamine, 0.05 mM 2-mercaptoethanol, and 10% DMSO.

Any non-resetting BMCs were left to adhere for two hours at 37° C. on tissue culture plates. Non-adherent cells were discarded, and adherent cells cultured for seven days in the presence of IL-4 (50 U/ml), and GM-CSF (100 ng/ml). The resulting population was enriched for antigen presenting cells ("APCs"; in this case, dendritic cells or macrophages). Then, from 5×10$^5$ to 10$^6$ of these cells were incubated in 2 ml wells for four hours, at 37° C., in 400 ul Iscove's medium supplemented with 2.5 ug/ml of human β2 microglobulin, and 50 ug/ml of the peptide of SEQ ID NO: 17. Adherent, peptide pulsed cells were then irradiated at 5000 rads, and washed. Next, 2×10$^6$ autologous CD8$^+$ T cells were added, in culture medium, supplemented with 1000 U/ml of IL-6, and 5 ng/ml of IL-12.

Seven days later, lymphocytes were restimulated with adherent, autologous BMCs, pulsed with peptide as above. 5×10$^6$ BMCs were left to adhere for two hours at 37° C., in 400 ul Iscove's medium containing β2-microglobulin and SEQ ID NO: 17, as discussed above. Any peptide pulsed, adherent cells, were irradiated and washed. Responder cells were then added, in culture medium supplemented with 10 U/ml of IL-2, and 5 ng/ml of IL-7.

On day 14, the lymphocytes were restimulated with autologous BMCs pulsed with SEQ ID NO: 17. The BMCs were incubated, at $2 \times 10^7$ cells/ml, in the Iscove's medium containing $B_2$-microglobulin and SEQ ID NO: 17. After two hours of incubation (20° C.), peptide pulsed BMCs were irradiated, washed, and resuspended at $2 \times 10^6$ cells/mi in culture medium augmented with IL-2 and IL-7, as above. Samples of these stimulator cells ($2 \times 10^6$), were added to each well which contained responder cells.

The responder lymphocytes were cloned on day 21. Anywhere from 10 to 0.3 cells/well were seeded in microwells, in culture medium which had been supplemented with 50 U/ml of IL-2, and 5 U/ml of IL-4. These were then stimulated by adding allogenic EBV transformed B cells (LG2-EBV-B) and irradiated at 10,000 rads, at 20,000 cells per well, and one of (i) peptide pulsed HLA-B4402$^+$ cells, or (ii) peptide pulsed HLA-B4403$^+$ cells. For (i) or (ii), irradiation was at 15,000 rads, at 8000 cells per well.

Microcultures were restimulated every week in the same way they were on the 21st day. The one change was that at days 28 and 35, 40,000 and 60,000 EBV-B cells, respectively, were added per well, as compared to 20,000 at day 21.

Between days 41 and 52, aliquots of the proliferating microcultures were transferred into V-bottom microwells, in order to test for lytic activity against HLA-B4402$^+$ or HLA-B4403$^+$ target cells, pulsed and not pulsed with SEQ ID NO: 17.

Any microcultures which showed anti-peptide lytic activity were restimulated with $5 \times 10^4$ irradiated, peptide-pulsed B4402$^+$ or B4403$^+$ cells, plus $5 \times 10^5$ irradiated LG2-EBV-B cells, in 800 ul of culture medium augmented with 50 U/ml of IL-2, and 5 U/ml of IL-4.

After seven days, the CTL clones were restimulated every week with $2 \times 10^5$ irradiated peptide pulsed B4402$^+$ or B4403$^+$ cells, together with $10^6$ irradiated LG2-EBV-B cells, as described supra. In this way, CTLs LB 816-CTL-340 A/1, and LB822-CTL-346A/1 were obtained. These CTLs are specific for complexes of SEQ ID NO: 17 and either HLA-B*4402, or HLA-B4403, respectively.

EXAMPLE 15

In a further set of experiments, HLA-B4402$^+$ or HLA-B4403$^+$ EBV-transformed B cells which do not express MAGE-3 were labelled with $^{51}$Cr in the presence of monoclonal antibody W6/32, for 1 hour, at 37° C., Brodsky, et al, J. Immunol 128: 129–135 (1982). The cells were washed, and incubated for 30 minutes at 20° C. in serum free medium, using varied concentrations of SEQ ID NO: 17. Each CTL described in Example 14 was tested in a $^{51}$Cr release assay, also as described, with chromium release being measured after four hours.

Figure 12A:
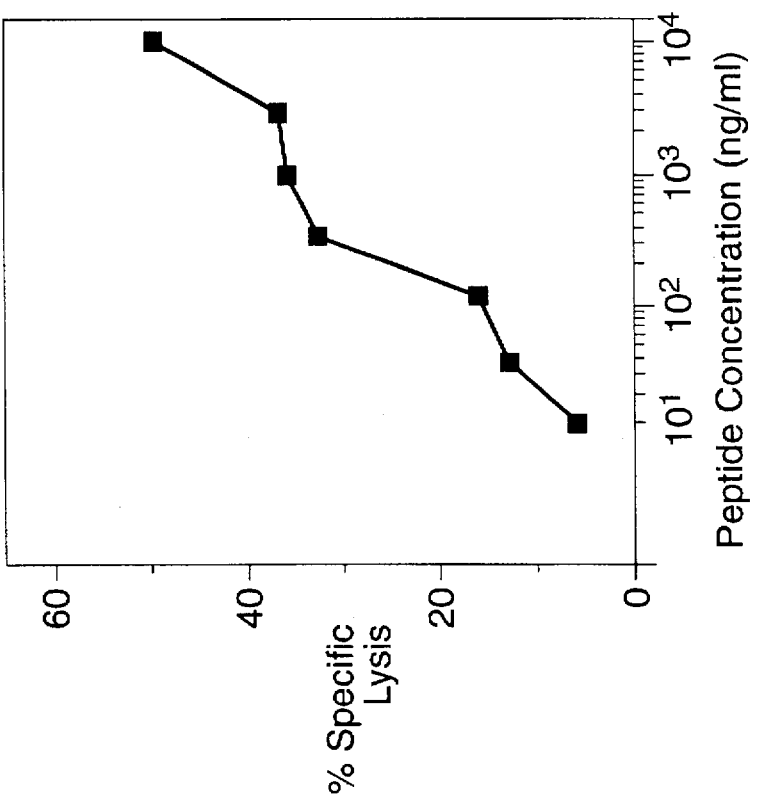
FIG. 12 depicts the result obtained when SEQ ID NO: 17 was used in connection with cells which naturally present HLA-B44, in $^{51}$Cr release assays.
Figure 12B:
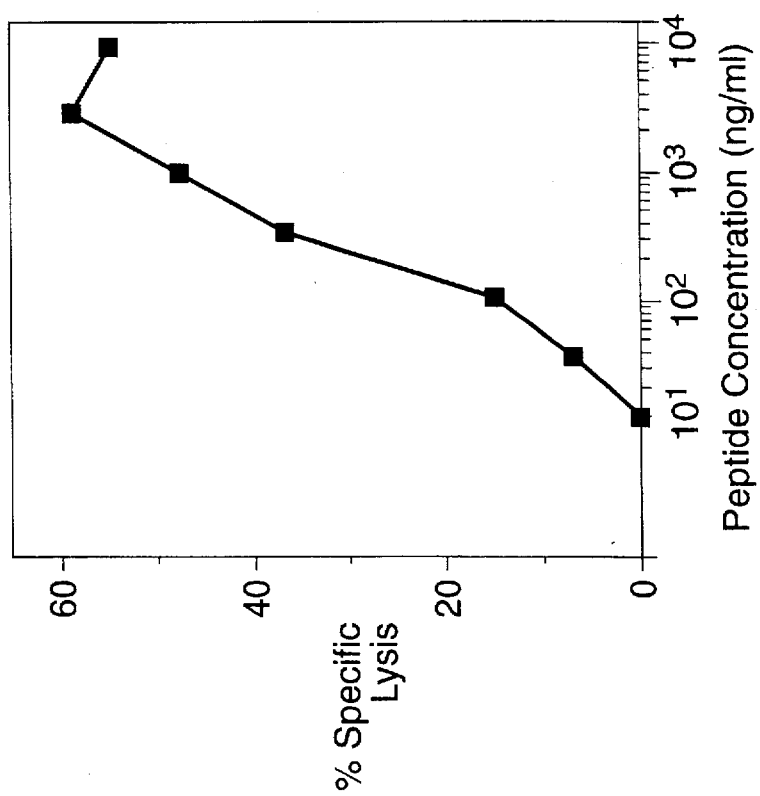

The results, set forth in FIG. 12, shows that the peptide did, in face, provoke lysis.

EXAMPLE 16

In the following experiments, additional tumor cell lines which are HLA-B44 positive were examined.

Figure 13A:
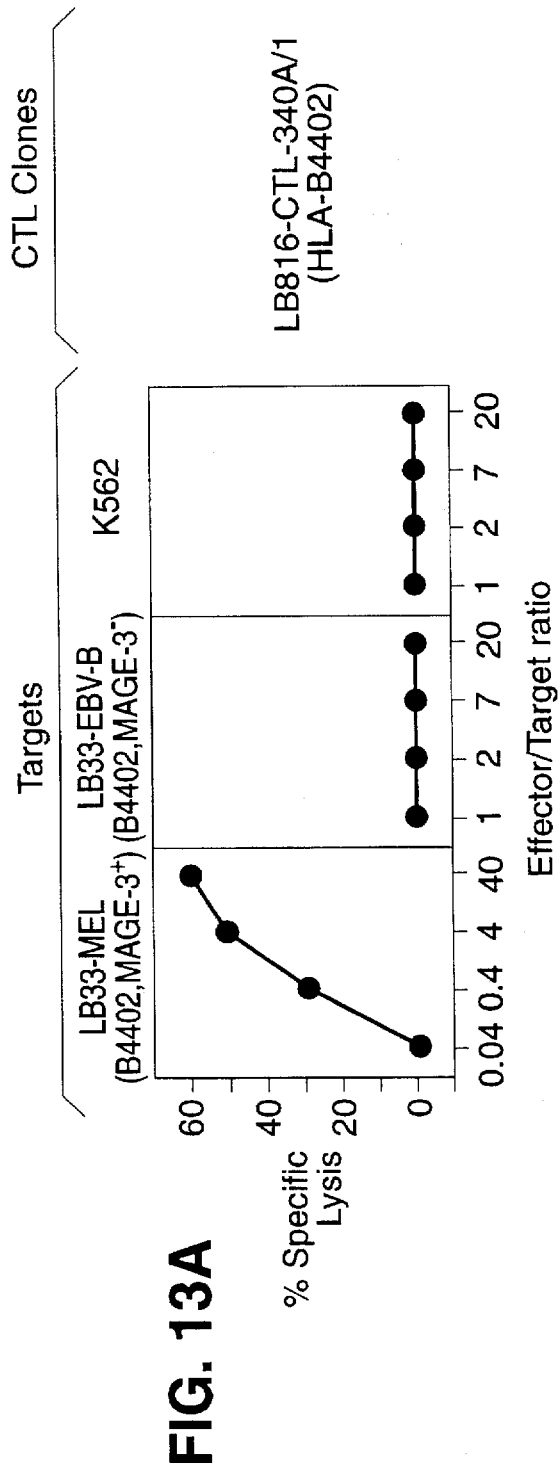
FIG. 13A and B summarize the results of $^{51}$Cr lysis assays where the target cells were naturally HLA-B44 positive, such as cancer cell lines.
Figure 13B:
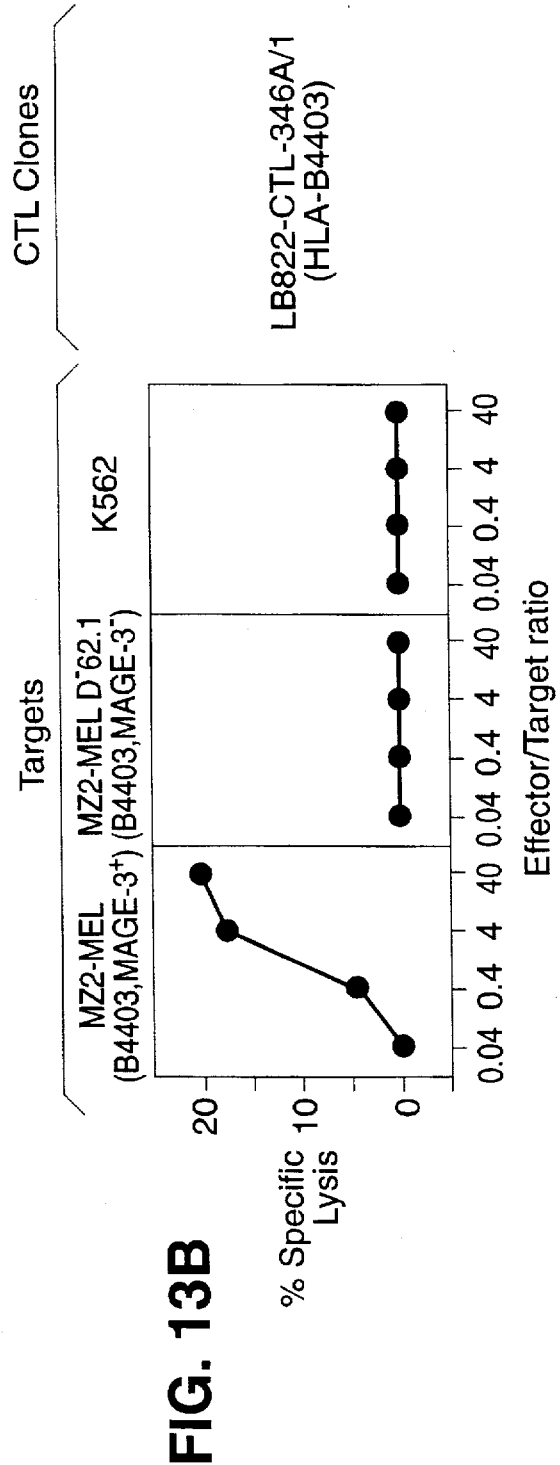

All cell lines tested were labelled with $^{51}$Cr for one hour, at 37° C. They were then added in Iscove's medium plus 2% fet al calf serum, to various accounts of the two CTL clones discussed in example 14. The amount of $^{51}$Cr released was measured after four hours. Controls were also used, as indicated in FIG. 13. Note that the cell line LB33-MEL was incubated with IFN-γ (50 U/ml), for 48 hours before the assay.

The results of these experiments are shown in FIG. 13. CTL clones LB816-CTL-340 A/1 and LB822-CTL-346 A/1 lysed tumor cells expressing MAGE-3, but did not lyse LB33-EBV B cells which did not express the MAGE gene. The CTL clone LB822-346 A/1 lysed the HLA-B*4403$^+$ tumor cell line MZ2-MEL, which expresses MAGE-3, but did not lyse the antigen loss variant MZ2-MEL.61.2D$^-$.

EXAMPLE 17

As a final test to determine if the peptide of SEQ ID NO: 17, in complexes with HLA-B44, stimulated CTLs, experiments were carried out to determine if tumor necrosis factor release was stimulated.

First, COS-7 cells were transfected by cDNA encoding MAGE-3 following Gaugler, et al, J. Exp. Med 179: 921–930 (1994), in the expression vector pcDNA-I/AMP, and one of HLA-B*4402 cDNA cloned into vector pcDNA3, or HLA-B*4403 cDNA cloned into pcDNA-I/AMP. The DEAE dextran chloroquine method of Aruffo, Proc. Natl. Acad. Sci. USA 84: 3365–3369 (1987) was used.

Transfectants were incubated for 24 hours, at 37° C., then 3000 CTLs/well were added. Materials were incubated for 18 hours, at 37° C. Supernatants were then collected, and TNF content was determined by testing the cytolytic effect on TNF sensitive WEHI-16 clone 13 cells, following Espevik et al, J. Immunol. Meth 95: 99–105 (1986).

Table 3, which follows, shows the results, wherein TNF release is expressed in pg/ml. LB33-MEL and LB494-MEL were incubated with IFN$_\gamma$ at 100 U/ml for 24 hours prior to the assay. Tumor cell lines LB33-MEL, LB494-MEL, and MZ2-MEL were also tested. These cell lines all express MAGE-3 cDNA, and are either HLA-B,4402$^+$ (LB33-MEL, LB494-MEL), or HLA-B*4403$^+$ (MZ2-MEL). Hence, no transfection was necessary for these cells. The results show that TNF was released. Hence, one concludes that SEQ ID NO: 17 is being presented by HLA-B44MHC molecules, and these complexes provoke CTL activity.

TABLE 3

| TNF production of anti-MAGE-3.B44 CTL clones | | |
|---|---|---|
| CTL Clones | Stimulator cells | TNF (pg/ml) |
| A LB816-CTL-340A/1 (B4402) | COS | 0.7 |
| | COS+MAGE-3 | 0.6 |
| | COS+HLA-B4402 | 0.5 |
| | COS+HLA+B4402+MAGE-3 | 33.7 |
| | LB33-MEL (B4402, MAGE-3$^{+++}$) | 74.9 |
| | LB494-MEL (B4402, MAGE-3$^{+++}$) | 32.3 |
| B LB822-CTL-346A/1 (B4403) | COS | 1.2 |
| | COS+MAGE-3 | 1 |
| | COS+HLA-B4403 | 1.2 |
| | COS+HLA-B4403+MAGE-3 | 26.6 |
| | MZ2-MEL (B4403, MAGE-3$^{+++}$) | 67.3 |

EXAMPLE 18

The results presented supra, taken with data presented by, e.g. Brichard, et al., Eur. J. Immunol. 26: 224–230 (1996) Buseyne, et al., J. Virol 67: 694–702 (1993); Coulie, et al., Proc. Natl. Acad. Sci. USA 91: 2105–2109 (1994); DiBrino, et al., Biochemistry 34: 10130–10138 (1995); Fleischhauer, et al., Tissue Antigens 44: 311–317 (1994); Khanna, et al., J. Exp. Med. 176: 169–176 (1992); Kita, et al., Hepatology 18: 1039–1044 (1993), show that peptides which bind to HLA-B44 molecules often contain Glu at position 2, and either Tyr or Phe in the last position. Analysis of the MAGE-3 sequence reveals that four peptide sequences satisfy these constraints, i.e.:

Gln Glu Glu Gly Pro Set Thr Phe (SEQ ID NO: 20);
Met Glu Val Asp Pro Ile Gly His Leu Tyr (SEQ ID NO: 17);
Trp Glu Glu Leu Ser Val Leu Glu Val Phe (SEQ ID NO: 21);
Glu Glu Leu Set Val Leu Glu Val Phe (SEQ ID NO: 22).

These peptides were synthesized using standard, solid phase techniques and were then used in experiments to determine if they bound to HLA-B44 MHC molecules.

The cells used in the experiments were C1R cells which had been transformed with Epstein Barr Virus (EBV). These cells differ from other, EBV transformed B cells in that they express the MAGE-3 gene. They are also MHC negative, and hence can serve as subjects for transfection with genes encoding MHC molecules. Samples were transfected with either of a cDNA molecule encoding HLA-B*4402, or with genomic DNA encoding HLA-B*4403 in accordance with Fleischhauer, et al., Tissue Antigens 44: 311–317 (1994) or Fleischhauer, et al., N. Eng. J. Med 323: 1828–1822 (1990) both of which are incorporated by reference. The transfectants were grown in RPMI-1640 medium which had been supplemented with 10% fetal calf serum (FCS).

In the competitive assay, the peptide

Glu Glu Lys Leu Ile Val Val Ala Phe (SEQ ID NO: 18) was used, as it has been reported to bind HLA-B44. See, e.g., Coulie, et al., Proc. Natl. Acad. Sci. USA 92: 7976–7980 (1995), incorporated by reference. Cytolytic T cell clone LB33-CTL-159/5 was also reported to recognize and to lyse cells presenting complexes of the peptide and HLA-B44 on their surface. This clone was used in the assay, together with a constant amount of SEQ ID NO: 18 together with varying amounts of each of SEQ ID NOS: 20, 17, 21, 22 and the following control peptides:

Ser Glu Ile Trp Arg Asp Ile Asp Phe (SEQ ID NO: 3) and
Phe Leu Arg Gly Arg Ala Tyr Gly Leu (SEQ ID NO: 19)

To carry out the assay, the transfected C1R (C1R-B*4402 or C1R-B*4403) transformed cells were $^{51}$Cr labelled for one hour, at 37° C., in the presence of anti-human class-I MHC monoclonal antibody W6/32 (30% w/v of culture medium of the hybridoma cells), and washed three times. Labelled cells (1000 cells in 80 ul), were incubated in V bottom microwells for 30 minutes at 20° C., in serum free, X-VIVO 10 medium. Test peptides were added, at varying concentrations, as explained infra, followed by the addition of the peptide Glu Glu Lys Leu Ile Val Val Ala Phe (SEQ ID NO: 18) at 50 ng/ml in 40 ul of X-VIVO 10 medium for C1R-B*4402, and 160 ng/ml for C1R-B*4403. This peptide is known to bind to both HLA-B*4402 and HLA-B*4403 allotypes. (See, e.g., Coulie, et al., Proc. Natl. Acad. Sci. USA 92: 7976–7980 (1995)). The cells which had been stimulated with SEQ ID NO: 18 were incubated for 30 minutes at 20° C., and then washed in Iscove's medium containing 2% fetal calf serum. Then, CTL clone LB33-159/5, described by Coulie et al as recognizing and lysing cells which present complexes of SEQ ID NO: 18 and HLA-B44 on their surface, were added at 20,000 cells in 150 ul of Iscove's medium supplemented with 10% human serum.

The competitive peptides were added at varying concentrations, until lysis by CTL 159/5 was inhibited by 50%. Lysis was determined using the formula described supra. When no competitor peptide was used, lysis of C1R-B*4402 transformants was 58%, and that of C1R-B*4403 was 72%.

In the table that follows, SEQ ID NOS: 3 and 19 were used as controls. The former, i.e.:

Set Glu Ile Trp Arg Asp Ile Asp Phe (SEQ ID NO: 3) is derived from tyrosinase and is known to bind to both HLA-B*4402 and HLA-B*4403 (Brichard, et al., Eur. J. Immunol. (1995), while the latter, i.e.

Phe Leu Arg Gly Arg Ala Tyr Gly Leu (SEQ ID NO: 19) binds to HLA-B8 (Burrows, et al., J. Exp. Med. 171: 345–349 (1990)). The results, presented below, set forth the concentration, in uM, of peptide needed to inhibit lysis of C1R-B44 cells sensitized with SEQ ID NO: 8.

| Peptide | C1R-B*4402 | C1R-B*4403 |
| --- | --- | --- |
| SEQ ID NO: 20 | 60 | 15 |
| SEQ ID NO: 17 | 2 | 1 |
| SEQ ID NO: 21 | 80 | 7 |
| SEQ ID NO: 22 | 20 | 5 |
| SEQ ID NO: 3 | 1 | <1 |
| SEQ ID NO: 19 | >100 | >100 |

As will be seen, all of SEQ ID NOS: 17, 20, 21 and 22 did inhibit lysis of C1R-B44 cells, which indicates that they bind to HLA-B44 molecules. The peptide of SEQ ID NO: 17 was the best binder for both HLA-B*B4402 and MLA-B*4403. This is shown in FIG. 14, wherein SEQ ID NOS: 17, 19 and 3 and are plotted as a function of lysis versus concentration of competitor peptides.

In experiments not reported here, peptides homologous to SEQ ID NO: 17, and derived from the amino acid sequence of MAGE-1, 2, 4, 6 and 12 were also tested, and were found to bind the HLA-B44 molecule.

EXAMPLE 19

Once it was clear that various peptides did, in fact bind to HLA-B44 allotypes, it was of interest to determine if the peptides could be used to provoke cytolytic T cell clones specific to the complexes of the peptide and the MHC molecule.

In order to determine this, adherent peripheral blood mononuclear cells were isolated from a donor, referred to as LB816, who did not suffer from cancer, and who was HLA-B*4402 positive.

The adherent cells were isolated by first securing a sample of peripheral blood mononuclear cells ("PBMCs" hereafter), using density gradient centrifugation. T-lymphocytes were purified from the sample via rosetting, using 2-aminoethyl-isothiouronium bromide hydrobromide-treated sheep erythrocytes, in accordance with Mikamo, J. Immunol. Meth. 107: 189–196 (1988), incorporated by reference, and via labelling with anti-CD8 monoclonal antibodies coupled to magnetic microbeads, followed by sorting of the CD8$^+$ cells via passage in a magnetic field. The thus separated cells were frozen for storage. Any non-resetting PBMCs were left to adhere for two hours at 37° C. on NUNC tissue culture wells, with non-adherent cells being discarded.

The adherent cells were then cultured, for seven days, in the presence of IL-4 (50 U/ml), and GM-CSF (100 ng/ml), in RPMI medium supplemented with 10% FCS. GM-CSF and IL-4 are used in order to increase the proportion of dendritic cells in the culture. See Romani, et al., J. Exp. Med. 180: 83–93 (1994); Sailusto, et al., J. Exp. Med. 179: 1109–1118 (1994). When the cell populations were analyzed, those taken from donor LB816 were found, for the most part, to be CD11c+ and CD14+, while cells from donor LB822 were mostly CD11c+ and CD14−.

A total of from $5\times10^5$ to $5\times10^6$ of these antigen presenting cells were then incubated in 2 ml wells, for four hours at 37° C., in 400 ul of Iscove's medium supplemented with human β2 microglobulin (2.5 ug/ml), and 50 ug/ml of SEQ ID NO: 17. Following this, the cells were irradiated at 50 Gy, and washed. These cells were then used as stimulator cells on the autologous CD8+ cells discussed supra. Six cultures of autologous CD8+ wells were established. For each culture, $2\times10^6$ CD8+ cells were combined with culture medium (Iscove's medium plus 10% human serum, L-arginine, L-asparagine, L-glutamine, 0.05 mM2-mercaptoethanol, 1000 U/ml IL-6 and 5 ng/ml IL-12). On days 7 and 14, these responder cells were stimulated with the stimulator cells. To do this, on day 7 the PBMCs ($5\times10^6$) were left to adhere for 2 hours, at 37° C. in 400 ul of Iscove's medium containing β2 microglobulin, and the peptide of SEQ ID NO: 17, as described supra. The adherent cells were irradiated and washed, also as described supra. The responder lymphocytes (i.e., the CD8+ cells), were added in culture medium which had been augmented with 10 U/ml of IL-2 and 5 ng/ml of IL-7. On day 14, the lymphocytes were restimulated with PBMCs which had been pulsed with peptide. In this restimulation, $2\times10^7$ PBMCs per ml were incubated for two hours at 20° C. in Iscove's medium with β2 microglobulin, and the peptide of SEQ ID NO: 17, as described supra. Again, these PBMCs were irradiated, washed, and resuspended at $2\times10^6$ cells/ml in culture medium supplemented with IL-2 and IL-7, and, again as described, were added to the responders.

Figure 15A:
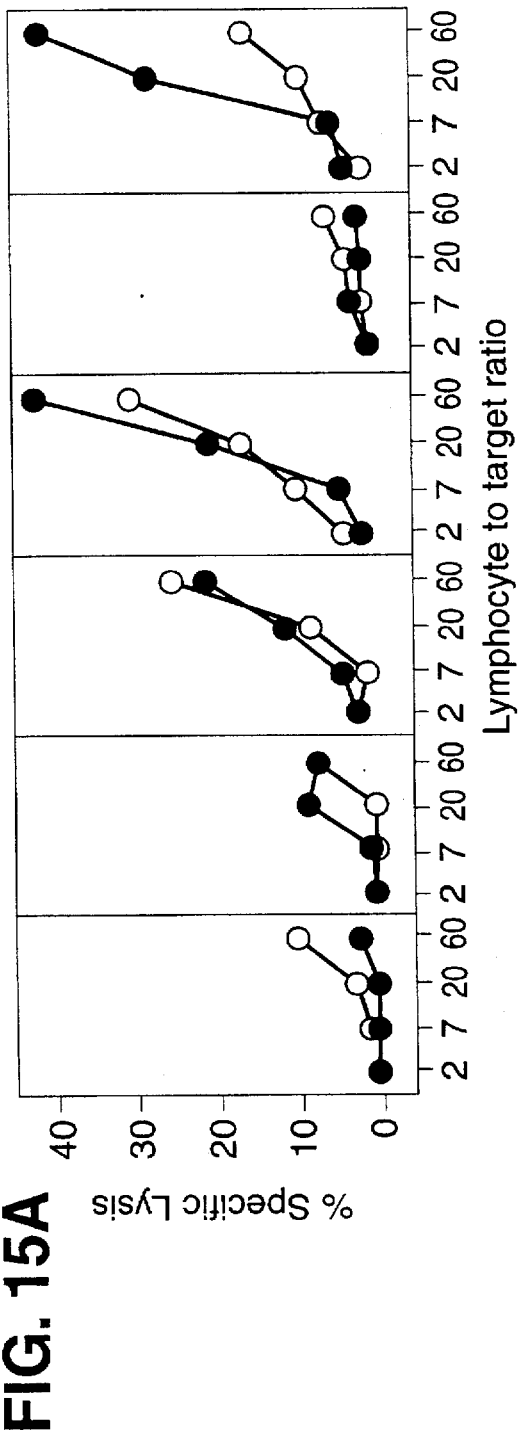
FIG. 15A shows the result of lytic assays, in a $^{51}$Cr release assay, where lymphocytes obtained from donor LB816 were tested against HLA-B*4402 presenting cells.

At day 20 the lyric activity was assessed on LB816 cells (HLA-B*4402 positive cells), which had been sensitized with SEQ ID NO: 17. The lytic activity was measured using the $^{51}$Cr release assay as described supra. The results are shown in FIG. 15A. Effector cells were incubated with unlabelled K562 target cells (50,000 cells/well) for 45 minutes, in order to inhibit lysis by NK-like effectors. $^{51}$Cr-labelled target cells (1000 cells/well) were incubated with 1 µM of SEQ ID NO: 17 (filled in circle) or without it (open circle). $^{51}$Cr release was measured after 4 hours. Only one of the six autologous CD8+ culture preferentially lysed the target cells.

Figure 15B:
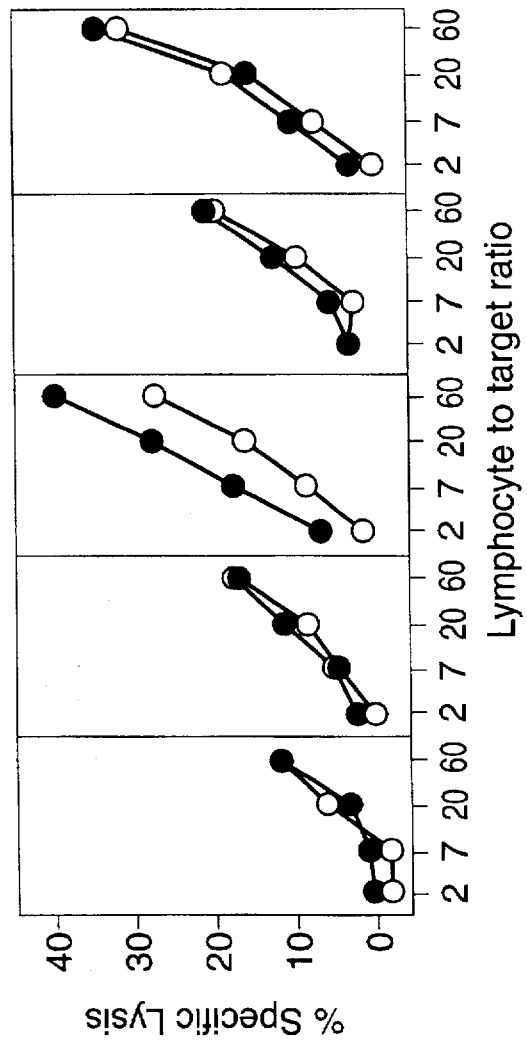
FIG. 15B presents parallel information, using lymphocytes obtained from donor LB822 CTL LB822, with HLA-B*4403 presenting cells.

Similarly, HLA-B*4403 positive cells (LB822), were tested. Results, presented in FIG. 15B, show that one out of five cultures tested preferentially lysed the cells.

Based upon these results, it was concluded that the frequency of precursors of anti-SEQ ID NO: 17/HLA-B44 cells was on the order of 1 out of every $10^7$ CD8+ lymphocytes.

The lymphocytes of the positive cultures were cloned by limiting dilution. Specifically, on day 21, these cells were cultured in culture medium supplemented with 50 U/ml of IL-2, and 5 U/ml of IL-4. The LB816 cells were stimulated with irradiated C1R-B*4402 cells (150 Gy, 8000 cells/ wells), which had been incubated for one hour at 20° C. with 1 ug/ml of SEQ ID NO: 17, and washed. The LB822 clones were stimulated with irradiated MZ2-MEL cells which are HLA-B*4403 positive melanoma cell (100 Gy, 8000 cells per well). Irradiated allogeneic LG2-EBV cells (100 Gy, 20,000 cells/well) were added as feeder cells. Microcultures were stimulated each week. CTL clones LB816-CTL-340/1 and LB822-CTL-346/8 were isolated in this fashion.

EXAMPLE 20

The CTL clones discussed supra were stimulated each week in 2 ml wells with $2\times10^5$ irradiated C1R-B*4402 or C1R-B*4403 cells, which had been incubated for one hour at 20° C. with 1 ug/ml of the peptide of SEQ ID NO: 17, then washed, and with $10^6$ irradiated LG2-EBV cells, all in culture medium supplemented with IL-2 and IL-4, as before.

In order to confirm that the CTL clones thus isolated recognized complexes of SEQ ID NO: 17, and both allotypes of HLA-B44, 10,000 cells of each CTL clone (per well) were combined with 1000 cells (per well), of $^{51}$Cr labelled lymphoblastoid B cells (LB33-EBV, which is HLA-B*4402 positive), which had been incubated, for 30 minutes, at 20° C. in serum free medium, with a varying concentration of SEQ ID NO: 17, and then washed. Release of $^{51}$Cr was measured after four hours, using the methods described herein.

Figure 16A:
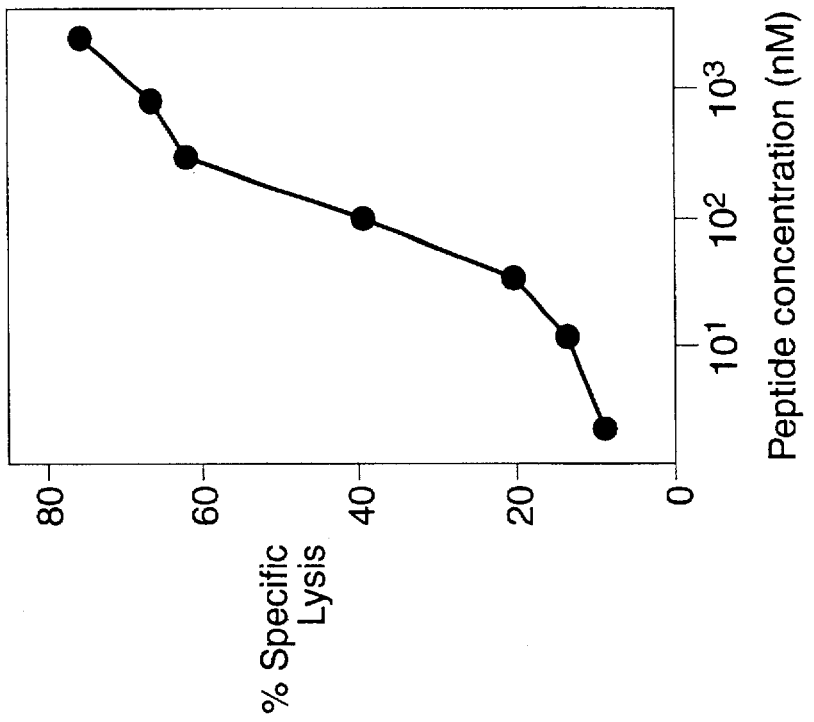
FIG. 16 presents data which confirm the specificity of CTLs specific for complexes of SEQ ID NO: 17 and HLA-B44 molecules.
Figure 16B:
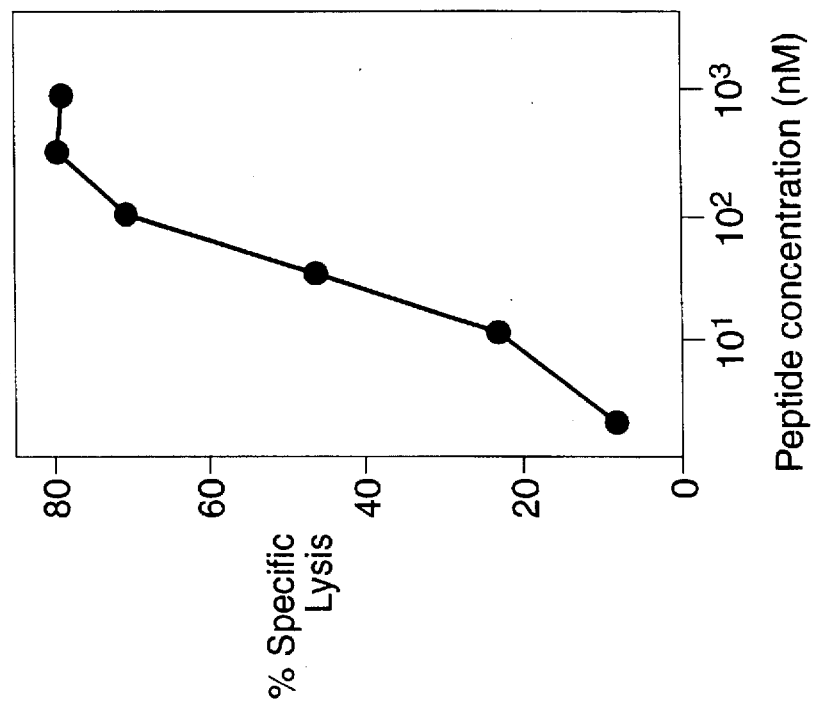

The results, shown in FIG. 16, demonstrate that, for CTL 340/1, half maximal lysis was obtained at approximately 40 nM, while half maximal lysis was obtained for CTL 346/8 at about 100 nM.

In experiments only summarized here, a peptide homologous to SEQ ID NO: 17 but for a difference at position 9 (where leucine/was replaced by valine) was tested. This peptide is from MAGE-6. It bound efficiently to both HLA-B44 subtypes, although the specific CTL clones being considered did not recognize it. Thus, for purposes of binding HLA-B44 molecules, the ninth position was not essential.

EXAMPLE 21

A further set of experiments were carried out to determine if SEQ ID NO: 17 was naturally presented on cells which express the MAGE-3 gene.

To determine this, COS-7 cells (15,000 per well) were cotransfected with 50 ng of pcDNA-I/Amp containing cDNA for MAGE-3, and either 50 ng of pcDNA-I/Amp containing cDNA for HLA-B*4403, or 50 ng of pcDNA3/ Amp containing cDNA for HLA-B*4402. The cotransfection was carried out in accordance with the well known protocol of Seed, et al., Proc. Natl. Acad. Sci. USA 84: 3365–3369 (1987). Also, NA8-MEL melanoma cells were cotransfected. These cells do not express either of HLA-B44 or MAGE-3 molecules. To cotransfect NA8-MEL (30,000 cells per well) 100 ng samples of the plasmids given supra were used, using LIPOFECTAMINE.

Following cotransfection, cells were incubated for 36 hours at 37° C., and then tested for their ability to stimulate production of tumor necrosis factor (TNF), in the presence of the CTL clones 340/1 and 346/8, discussed supra. TNF production was determined following Lehmann et al., Eur. J. Immunol. 25: 340–347 (1995), incorporated by reference, but discussed briefly here. in these experiments, 3000 CTLs were added in 100 ul of Iscove's medium supplemented with 10% human serum, and 25 U/ml of IL-2. After 20 hours, supernatant was collected and TNF content determined by testing its cytotoxicity on WEHI 164c13 cells, in accordance with Espevik et al., J. Immunol. Meth. 95: 99–105 (1986). In these experiments, summarized in FIG. 17, controls were prepared using single transfections (either MAGE-3 or HLA-B*4402 or HLA-B*4403).

Figure 17:
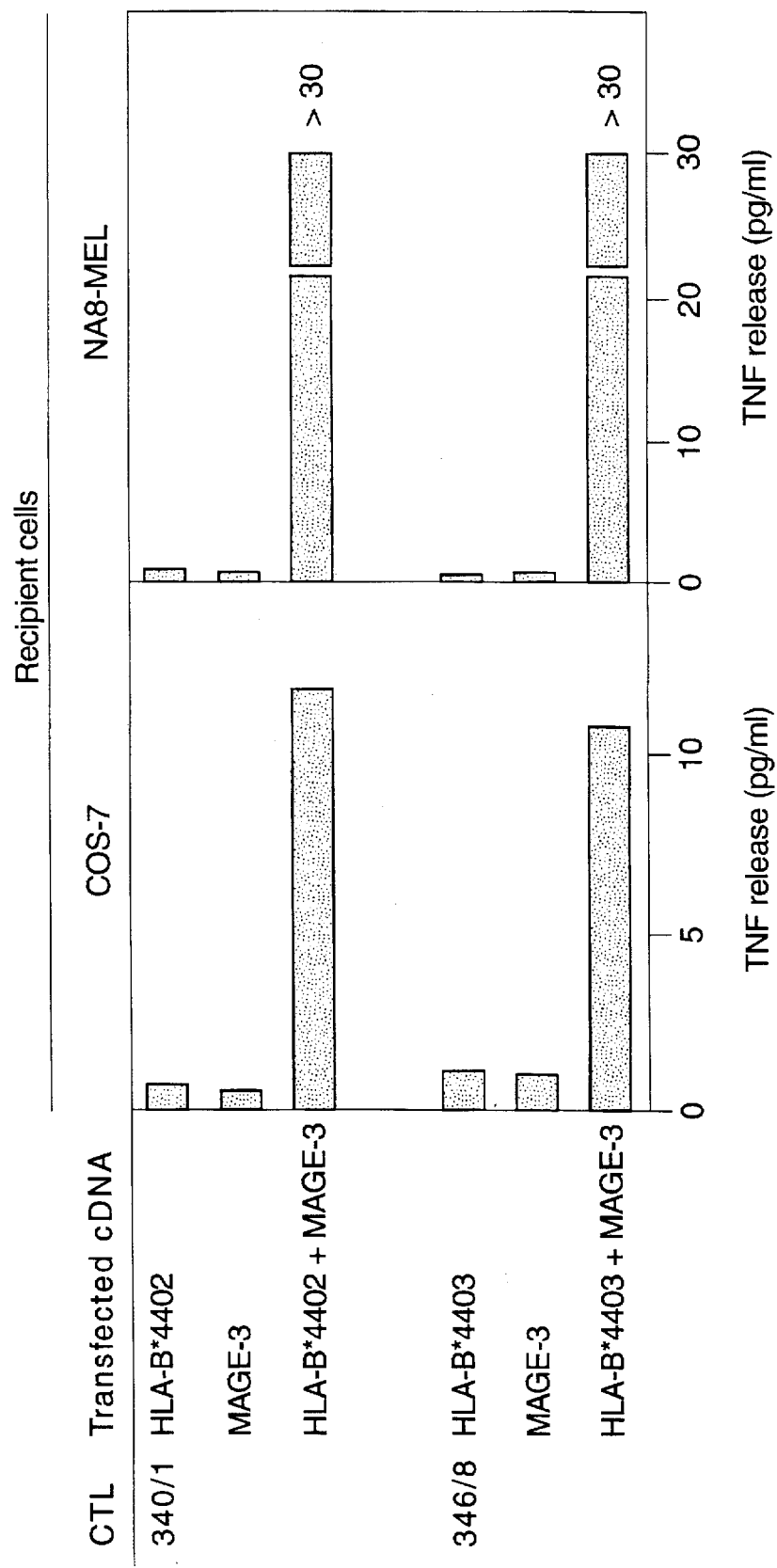
FIG. 17 presents data which confirm the specificity of CTLs specific for MAGE-3 and HLA-B44.

FIG. 17 shows that cells cotransfected with the two constructs stimulated TNF release, while cells transfected with one plasmid did not. This result was observed with both cell types, and both CTLs. The recognition of MAGE-3/ HLA-B44 complexes did not require the high copy number provided by COS-7 cells, as the NA8-MEL work shows.

EXAMPLE 22

Figure 18A:
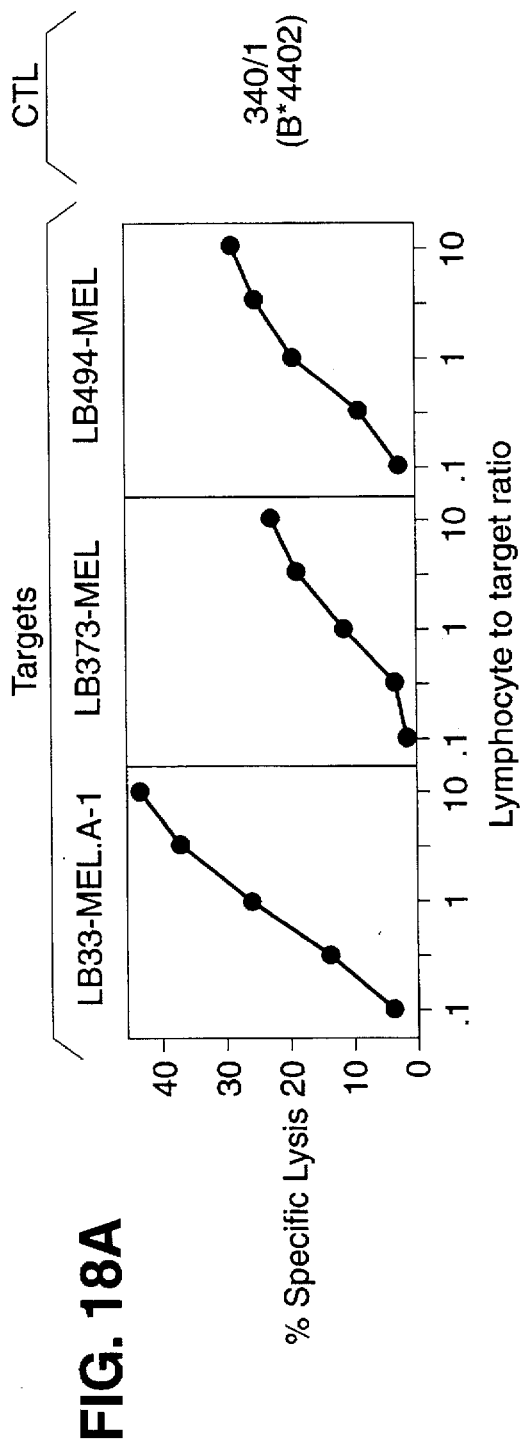
FIG. 18A and B summarize results obtained when cells which naturally present HLA-B44 molecules and also express MAGE-3 were tested with the CTLs discussed in this application.
Figure 18B:
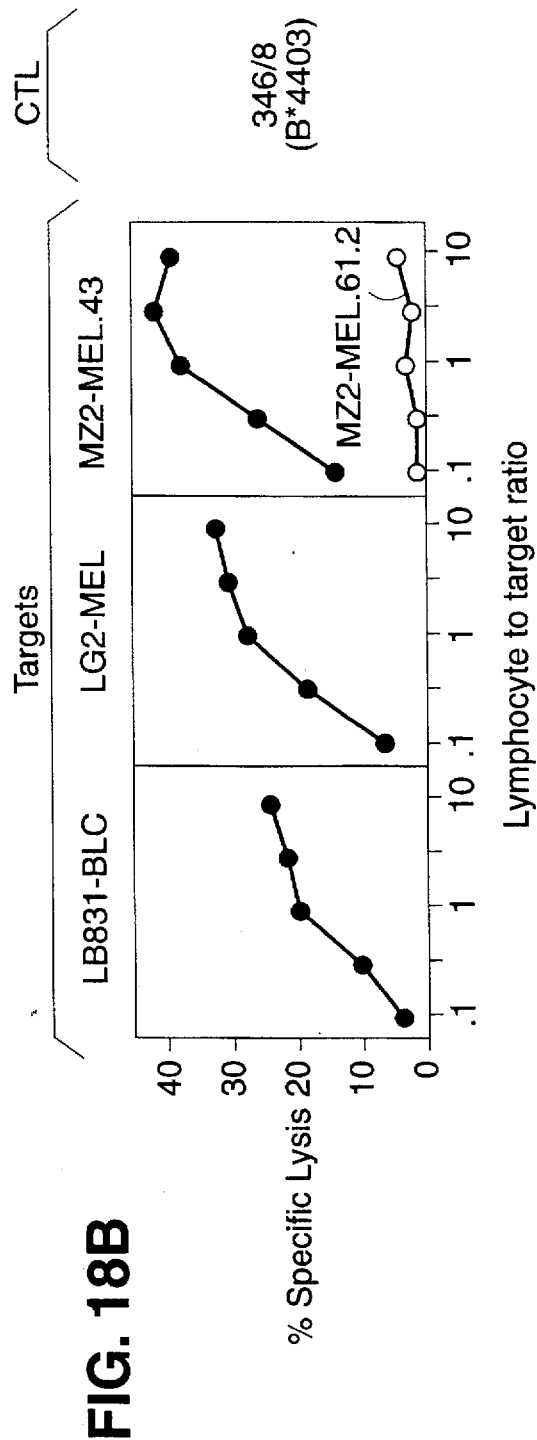

The CTLs described supra, i.e., 340/1 and 346/8, were then tested for their ability to lyse HLA-B44 presenting tumor cells. The cells used included lines known to express MAGE-3, including LB33-MEL-A-1, LB373-MEL, LB494-MEL, LB831-BLC, LG2-MEL and MZ2-MEL.43, which are melanoma cells except for LB831-BLC, which is a bladder cancer derived cell line. Cell line MZ2-MEL.61.2 is a melanoma cell line which has lost expression of MAGE-3. In FIG. 18, which is discussed infra, this cell is depicted by open ("○") circles, rather than closed ("●") circles. All cells, with the exception of MZ2-MEL.43, MZ2-MEL.61.2, and LG2-MEL were incubated, over 48 hours, in the presence of 50 U/ml of IFN-γ, prior to use in a $^{51}$Cr release assay. In each case, the expression of HLA-B*4403, or HLA-B*4403, and MAGE-3 was tested, using RT-PCR methodologies not repeated here.

The results, set forth in FIG. 18, show that the CTLs did recognize and lyse these naturally MAGE-3/HLA-B44 expressing cells. The foregoing experiments describe isolated nucleic acid molecules coding for a tumor rejection antigen precursor, a "TRAP" molecule. The protein molecule for which these code is processed intracellularly in a manner which leads to production of at least one tumor rejection antigen, or "TRA", which is presented by HLA-B44 molecules. While it has been observed previously that HLA-B44 molecules present peptides derived from tyrosinase, the nucleic acid molecules of the invention do not code for tyrosinase, and the TRAs are not tyrosinase derived.

The tumor rejection antigens of the invention are isolated nonapeptides which have a Glu residue at the 2nd position, and a Phe or Tyr residue at the 9th or 10th position. Especially preferred are peptides which satisfy the following formula:

Xaa Glu Xaa Asp Xaa Xaa Xaa Xaa Xaa Tyr (SEQ ID NO: 23) or

Xaa Glu Xaa Val Xaa Xaa Xaa Xaa Xaa Tyr (SEQ ID NO: 24)

wherein Xaa is any amino acid. These generic formulas embrace SEQ ID NO: 17, as well as homologous peptides derived from different MAGE proteins which, as has been discussed, supra, also bind to HLA-B44 molecules. These homologous include:

Lys Glu Ala Asp Pro Thr Gly His Ser Tyr (SEQ ID NO: 25);

Val Glu Val Val Pro Ile Ser His Leu Tyr (SEQ ID NO: 26);

Lys Glu Val Asp Pro Ala Ser Asn Thr Tyr (SEQ ID NO: 27);

Met Glu Ala Asp Pro Thr Ser Asn Thr Tyr (SEQ ID NO: 28)

Met Glu Val Asp Pro Ile Gly His Val Tyr (SEQ ID NO: 29); and

Val Glu Val Val Arg Ile Gly His Leu Tyr (SEQ ID NO: 30).

These correspond to peptide sequences which are homologous to SEQ ID NO: 17, in that they are found at the corresponding positions of MAGE-1, 2, 4, 5, 6 and 12, respectively. Their ability to bind to HLA-B44 molecules renders them useful, inter alia, in identifying cells which present HLA-B44 molecules in their surfaces.

The peptides of the invention are similar to the peptide disclosed in Ser. No. 08/233,305, now U.S. Pat. No. 5,519, 117 co-assigned to the assignee of the subject application, i.e.:

Ser Glu Ile Trp Arg Asp Ile Asp Phe (SEQ ID NO: 3)

Khanna, et al., supra, teaches a decamer, i.e.:

Glu Glu Asn Leu Leu Asp Phe Val Arg Phe (SEQ ID NO: 4) but does not discuss how modification of the decamer could lead to an effective nonamer.

The invention thus involves tumor rejection antigens which bind to HLA-B44 molecules, and then provoke lysis by CTLs.

As indicated, the complexes of TRA and HLA molecule provoke a cytolytic T cell response, and as such isolated complexes of the tumor rejection antigen and an HLA-B44 molecule are also encompassed by the invention, as are isolated tumor rejection antigen precursors coded for by the previously described nucleic acid molecules. Given the binding specificity, the peptides may also be used, simply to identify HLA-B44 positive cells.

The invention as described herein has a number of uses, some of which are described herein. First, the identification of a tumor rejection antigen which is specifically presented by an HLA-B44 molecule, as well as a nucleic acid molecule coding for its parallel tumor rejection antigen precursor permits the artisan to diagnose a disorder characterized by expression of the TRAP. These methods involve determining expression of the TRAP gene, and/or TRAs derived therefrom, such as TRA presented by HLA molecules. Other TRAs may also be derived from the TRAPs of the invention and presented by different HLA molecules. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred.

The isolation of the TRAP gene also makes it possible to isolate the TRAP molecule itself, especially TRAP molecules containing the amino acid sequence of SEQ ID NO: 1. Fragments of peptides of these isolated molecules when presented as the TRA, or as complexes of TRA and HLA-B44, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and MLA, may be used to produce antibodies, using standard techniques well known to the art.

When "disorder" is used herein, it refers to any pathological condition where the tumor rejection antigen precursor is expressed. An example of such a disorder is cancer, melanoma in particular. Therapeutic approaches based upon the disclosure are premised on a response by a subject's immune system, leading to lysis of TRA presenting cells, such as cells presenting the relevant HLA molecule. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 7, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated, cytolytic T cell clone which is specific for complexes of SEQ ID NO: 17 and an HLA-B44 molecule.

2. The isolated, cytolytic T cell clone of claim 1, wherein said HLA-B44 molecule is an HLA-B*4402 molecule.

3. The isolated, cytolytic T cell clone of claim 1, wherein said HLA-B44 molecule is an HLA-B*4403 molecule.

* * * * *

UNITED STATES PATENT AND TRADEMARK OFFICE
CERTIFICATE OF CORRECTION

Page 1 of 3

PATENT NO. : 5,744,353
DATED : April 28, 1998
INVENTOR(S) : Jean Herman, et al.

It is certified that error appears in the above-identified patent and that said Letters Patent is hereby corrected as shown below:

In column 2, line 29, change "5,437,974" to -- 5,487,974 --.
In column 2, line 44, change "5,579,117" to -- 5,519,117 --.
In column 2, line 63, change "int." to -- Int. --.
In column 3, line 36, change "antigens" to -- antigen --.
In column 3, line 50, change "LBB33" to -- LB33 --.
In column 4, line 9, change "FIG" to -- FIGS --.
In column 4, line 39, change "FIG" to -- FIGS --.
In column 4, line 55, change "FIG" to -- FIGS --.
In column 6, line 42, change "Dulbeco's" to -- Dulbecco's --.
In column 7, line 1, change "soura" to -- supra --.
In column 7, line 38, change "100-200 ng/m" to -- 100-200 ng/ml --.
In column 7, line 43, change "Melc1" to -- MELc1 --.
In column 8, line 22, change "$A^+B^+C^+D^+$" to -- $A^+B^-C^+D^+$ --.
In column 8, line 24, change "$A^+B^+C^+D^+$" to -- $A^+B^-C^-D^+$ --.
In column 9, line 18, change "LBBB-MEL.A-1" to -- LB33-MEL.A-1 --.
In column 9, line 56, change "haplotype" to -- haplotypes --.

UNITED STATES PATENT AND TRADEMARK OFFICE
CERTIFICATE OF CORRECTION

Page 2 of 3

PATENT NO. : 5,744,353
DATED : April 28, 1998
INVENTOR(S) : Jean Herman, et al.

It is certified that error appears in the above-identified patent and that said Letters Patent is hereby corrected as shown below:

In column 12, line 51, change "non-resetting" to -- non-rosetting --.
In column 13, line 1, change "microglobuiin" -- microglobulin --.
In column 13, line 11, change "cells/mi" to -- cells/ml --.
In column 13, line 33, change "lyric" to -- lytic --.
In column 14, line 39, change " HLA-B, 4402$^+$ " to -- HLA- B*4402$^+$ --.
In column 15, line 9, change "Set" to -- Ser --.
In column 15, line 13, change "Set" to -- Ser --.
In column 16, line 9, change "Set" to -- Ser --.
In column 16, line 61, change "non-resetting" to -- non-rosetting --.
In column 17, line 2, change "Sailusto" to -- Sallusto --.
In column 17, line 20, change "microglobuiin" to -- microglobulin --.
In column 17, line 34, change "lyric" to -- lytic --.
In column 17, line 43, change "culture" to -- cultures --.
In column 17, line 60, change "cell" to -- cells --.
In column 18, line 21, after "leucine" delete -- / --.

UNITED STATES PATENT AND TRADEMARK OFFICE
CERTIFICATE OF CORRECTION

PATENT NO. : 5,744,353
DATED : April 28, 1998
INVENTOR(S) : Jean Herman, et al.

It is certified that error appears in the above-identified patent and that said Letters Patent is hereby corrected as shown below:

In column 18, line 49, change "in" to -- In --.
In column 19, line 29, change "cr" to -- or --.
In column 19, line 40, after "homologous" insert -- peptides --.

Signed and Sealed this

Thirty-first Day of October, 2000

Attest:

Q. TODD DICKINSON

*Attesting Officer*          *Director of Patents and Trademarks*

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
( A ) LENGTH: 1896 base pairs
( B ) TYPE: nucleic acid
( C ) STRANDEDNESS: single
( D ) TOPOLOGY: linear ( x i ) SEQUENCE DESCRIPTION: SEQ ID NO: 1:

```
GCGGCGGTGG  CGGAGGCGGA  CACATTGGCG  TGAGACCTGG  GAGTACGTTG  TGCCAAATCA        60

TTGCCACTTG  CCACATGAGT  GTAAATGATG  GCGGATGCAA  GTATGTCCTC  TGCCGATGGG       120

AAAAGCGATT  ATGGCCTGCG  AAGGTGACAG  CCATTATTCT  GTAACTTCAG  GACTTAGAAA       180

TGACTTTCGG  GTGACAAGTA  AAATCTTGAT  CAGGAGATAC  CTAGGATTTG  CTTCAGTGAA       240

ATAATTGAGC  CAGAACACGG  TTGGCACTGA  TTCTCGTTCC  CCATTTAATG  GGGTTTTGGT       300

CTAGTGCTTC  CAAGGTTACA  CTTCCAGAAA  TGTCTTTTTT  TTTTCACACT  AAAAAAAAAA       360

AAAAGAATCA  GCTGTAAAAA  GGCATGTAAG  GCTGTAACTC  AAGGAAAGAT  CTGGCAAGCA       420

GCCCTGTGAT  AGTAAATTAT  GGTCGTGTTC  AGGGAATGCT  TTCCAGCAAT  TCAGTAGACA       480

GTGCTCAGCT  GCAATGCAAA  AGCCCAGGTC  CTTGTCTTTG  TCTGCCACTG  GCCTCTCATG       540

CCTCAGTTTC  CCCATCTGTG  AAACAATGGG  GATTGGACCA  AATATCTGAA  ATCCATGGT       600

TATAGGCCTT  CAGGATTACC  TGCTGCATTT  GTGCTAAAGT  TTGCCACTGT  TTCTCACTGT       660

CAGCTGTTGT  AATAACAAGG  ATTTTCTTTT  GTTTAAATG   TAGGTTTTGG  CCCGAACCGC       720

GACTTCAACA  AAAAATAAGA  GAAGAAAGGA  ATATTTCTA   GCTGTGCAAA  TCCTCTCCCT       780

AGAGGAAAAG  TTAATTGTTG  TGTTGTTTTA  ATACTGTTTT  TTCCCGTGTA  GATTTCTGAT       840

ACTTCAATCC  CCTACTCCCC  CAAAACAGTT  GAAGCCCAGC  CCACTCTTAA  TGGGCTTATT       900
```

| | | | | | |
|---|---|---|---|---|---|
| CACCATTTGT | GTAATTCATT | AATGCTCATA | ATAACCTCAT | GAGAAAGCAA | CTAGTTTGAT | 960
| TTTATGTCAG | TTTGGAAGCT | GAAGATCCAA | ACGAGGCATT | CTGTGAGATC | TATGGAGAGA | 1020
| TTGGTACAAA | CACTGAATAC | ATGTAAATTA | TACTCAGGGT | AGACCCTATT | TGTGGTTAAA | 1080
| ATAGGGATAT | TTCCTTTTTT | TTTTTTTTTT | TTTGACTGT  | TTCTTAATCA | GTGCCATGCC | 1140
| AGGAAAATAG | GGATGTTTCC | TTCCCAGAGA | TCTGTGTGTC | TTTTTTCAGA | AACGTCTGTG | 1200
| ACAGGCCCAT | CAATTTTGAA | ATATTTGGTT | TTTGAGCCTG | TCACTCTAAA | CCAGCGTTTA | 1260
| ACGTTCAAAA | GGCAAATAAC | TGATGACCAG | GCGGCACATT | GTTCTGCTCC | GTGAGTGTCT | 1320
| GGCACTGGGA | AAGGTGTAGA | TTGTCTAGAA | TGACAGCAAT | CCGACGCCC  | CAGTCAGTCC | 1380
| TGCGTGATTG | TGGCGAGGGC | GCGTCTGGCA | CCGGGAAGGT | GTAGATCATC | TAGAATGACG | 1440
| GCGATTCCGA | CGCCCCGGTC | AGTCCTGCGT | GATTGGCGAG | GGTGCATCTG | TCGTGAGAAT | 1500
| TCCCAGTTCT | GAAGAGAGCA | AGGAGACTGA | TCCCGCGTAG | TCCAAGGCAT | GGCTCCCCT  | 1560
| GTTGCTCTTC | CTTGTGGAGC | TCCCCCTGCC | CCACTCCCTC | CTGCCTGCAT | CTTCAGAGCT | 1620
| GCCTCTGAAG | CTCGCTTGGT | CCCTAGCTCA | CACTTTCCCT | GCGGCTGGGA | AGGTAATTGA | 1680
| ATACTCGAGT | TTAAAAGGAA | AGCACATCCT | TTTAAACCAA | AACACACCTG | CTGGGCTGTA | 1740
| AACAGCTTTT | AGTGACATTA | CCATCTACTC | TGAAAATCTA | ACAAGGAGT  | GATTTGTGCA | 1800
| GTTGAAAGTA | GGATTTGCTT | CATAAAAGTC | ACAATTTGAA | TTCATTTTTG | CTTTTAAATC | 1860
| CAGCCAACCT | TTTCTGTCTT | AAAAGGAAAA | AAAAAA     |            |            | 1896

(2) INFORMATION FOR SEQ ID NO: 2:

(i) SEQUENCE CHARACTERISTICS:
        (A) LENGTH: 9 amino acid residues
        (B) TYPE: amino acids
        (D) TOPOLOGY: linear (xi) SEQUENCE DESCRIPTION: SEQ ID NO: 2:

Glu Glu Lys Leu Ile Val Val Leu Phe
                 5

(2) INFORMATION FOR SEQ ID NO: 3:

(i) SEQUENCE CHARACTERISTICS:
        (A) LENGTH: 9 amino acids
        (B) TYPE: amino acid
        (D) TOPOLOGY: linear (ii) MOLECULE TYPE: protein (ix) FEATURE:
        (A) NAME/KEY: HLA-B44 binding peptide (xi) SEQUENCE DESCRIPTION: SEQ ID NO: 3:

Ser Glu Ile Trp Arg Asp Ile Asp Phe
                 5

(2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: Khanna peptide (xi) SEQUENCE DESCRIPTION: SEQ ID NO: 4:

Glu Glu Asn Leu Leu Asp Phe Val Arg Phe
        5                          10

( 2 ) INFORMATION FOR SEQ ID NO: 5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: PCR primer ( x i ) SEQUENCE DESCRIPTION: SEQ ID NO: 5:

GCCGGAGTAT TGGGACGA                                                     18

( 2 ) INFORMATION FOR SEQ ID NO: 6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: PCR primer ( x i ) SEQUENCE DESCRIPTION: SEQ ID NO: 6:

GGCCGCCTCC CACTTGC                                                      17

( 2 ) INFORMATION FOR SEQ ID NO: 7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: PCR primer ( x i ) SEQUENCE DESCRIPTION: SEQ ID NO: 7:

GGAGTATTGG GACCGGAAG                                                    19

( 2 ) INFORMATION FOR SEQ ID NO: 8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: PCR primer ( x i ) SEQUENCE DESCRIPTION: SEQ ID NO: 8:

GGCCGCCTCC CACTTGT                                                      17

( 2 ) INFORMATION FOR SEQ ID NO: 9:

( i ) SEQUENCE CHARACTERISTICS:

(A) LENGTH: 18 base pairs
            (B) TYPE: nucleic acid
            (C) STRANDEDNESS: single
            (D) TOPOLOGY: linear (ii) MOLECULE TYPE: nucleic acid (ix) FEATURE:
            (A) NAME/KEY: PCR primer (xi) SEQUENCE DESCRIPTION: SEQ ID NO: 9:

CGCCACGAGT CCGAGGAT                                                                                    18

(2) INFORMATION FOR SEQ ID NO: 10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: nucleic acid (ix) FEATURE:
            (A) NAME/KEY: PCR primer (xi) SEQUENCE DESCRIPTION: SEQ ID NO: 10:

CCTTGCCGTC GTAGGCTA                                                                                    18

(2) INFORMATION FOR SEQ ID NO: 11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: nucleic acid (ix) FEATURE:
            (A) NAME/KEY: PCR primer (xi) SEQUENCE DESCRIPTION: SEQ ID NO: 11:

CGCCACGAGT CCGAGGAA                                                                                    18

(2) INFORMATION FOR SEQ ID NO: 12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: nucleic acid (ix) FEATURE:
            (A) NAME/KEY: PCR primer (xi) SEQUENCE DESCRIPTION: SEQ ID NO: 12:

CCTTGCCGTC GTAGGCGT                                                                                    18

(2) INFORMATION FOR SEQ ID NO: 13:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: nucleic acid (ix) FEATURE:

(A) NAME/KEY: PCR primer (xi) SEQUENCE DESCRIPTION: SEQ ID NO: 13:

CCGAGTGAAC CTGCGGAAA　　　　　　　　　　　　　　　　　　　　　　　　　　19

(2) INFORMATION FOR SEQ ID NO: 14:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: nucleic acid (ix) FEATURE:
  (A) NAME/KEY: PCR primer (xi) SEQUENCE DESCRIPTION: SEQ ID NO: 14:

GGTCGCAGCC ATACATCCA　　　　　　　　　　　　　　　　　　　　　　　　　　19

(2) INFORMATION FOR SEQ ID NO: 15:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: nucleic acid (ix) FEATURE:
  (A) NAME/KEY: PCR primer (xi) SEQUENCE DESCRIPTION: SEQ ID NO: 15:

TACAAGCGCC AGGCACAGG　　　　　　　　　　　　　　　　　　　　　　　　　　19

(2) INFORMATION FOR SEQ ID NO: 16:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: nucleic acid (ix) FEATURE:
  (A) NAME/KEY: PCR primer (xi) SEQUENCE DESCRIPTION: SEQ ID NO: 16:

CTCCAGGTAG GCTCTGTC　　　　　　　　　　　　　　　　　　　　　　　　　　18

(2) INFORMATION FOR SEQ ID NO: 17:

(i) SEQUENCE CHARACTERISTICS:
  (A) LENGTH: 10 amino acids
  (B) TYPE: amino acid
  (D) TOPOLOGY: linear (ii) MOLECULE TYPE: protein (ix) FEATURE:
  (A) NAME/KEY: Mage-3 peptide (xi) SEQUENCE DESCRIPTION: SEQ ID NO: 17:

Met Glu Val Asp Pro Ile Gly His Leu Tyr
     5       10

(2) INFORMATION FOR SEQ ID NO: 18:

(i) SEQUENCE CHARACTERISTICS:
    (A) LENGTH: 9 amino acids
    (B) TYPE: amino acid
    (D) TOPOLOGY: linear (ii) MOLECULE TYPE: protein (ix) FEATURE:
    (A) NAME/KEY:

(xi) SEQUENCE DESCRIPTION: SEQ ID NO: 18:

Glu Glu Lys Leu Ile Val Val Ala Phe
                 5

(2) INFORMATION FOR SEQ ID NO: 19:

(i) SEQUENCE CHARACTERISTICS:
    (A) LENGTH: 9 amino acids
    (B) TYPE: amino acid
    (D) TOPOLOGY: linear (ii) MOLECULE TYPE: protein (ix) FEATURE:
    (A) NAME/KEY:

(xi) SEQUENCE DESCRIPTION: SEQ ID NO: 19:

Phe Leu Arg Gly Arg Ala Tyr Gly Leu
                 5

(2) INFORMATION FOR SEQ ID NO: 20:

(i) SEQUENCE CHARACTERISTICS:
    (A) LENGTH: 8 amino acids
    (B) TYPE: amino acid
    (D) TOPOLOGY: linear (ii) MOLECULE TYPE: protein (ix) FEATURE:
    (A) NAME/KEY: Mage-3 peptide (xi) SEQUENCE DESCRIPTION: SEQ ID NO: 20:

Gln Glu Glu Gly Pro Ser Thr Phe
                 5

(2) INFORMATION FOR SEQ ID NO: 21:

(i) SEQUENCE CHARACTERISTICS:
    (A) LENGTH: 10 amino acids
    (B) TYPE: amino acid
    (D) TOPOLOGY: linear (ii) MOLECULE TYPE: protein (ix) FEATURE:
    (A) NAME/KEY: Mage-3 peptide (xi) SEQUENCE DESCRIPTION: SEQ ID NO: 21:

Trp Glu Glu Leu Ser Val Leu Glu Val Phe
                 5                   10

(2) INFORMATION FOR SEQ ID NO: 22:

(i) SEQUENCE CHARACTERISTICS:
    (A) LENGTH: 9 amino acids
    (B) TYPE: amino acid
    (D) TOPOLOGY: linear (ii) MOLECULE TYPE: protein -continued

```
    ( i x ) FEATURE:
            ( A ) NAME/KEY: Mage-3 peptide ( x i ) SEQUENCE DESCRIPTION: SEQ ID NO: 22:

Glu Glu Leu Ser Val Leu Glu Val Phe
                 5
```

( 2 ) INFORMATION FOR SEQ ID NO: 23:

```
    ( i ) SEQUENCE CHARACTERISTICS:
            ( A ) LENGTH: 10 amino acids
            ( B ) TYPE: amino acid
            ( D ) TOPOLOGY: linear ( i i ) MOLECULE TYPE: protein ( i x ) FEATURE:
            ( A ) NAME/KEY: HLA-B44 motif ( x i ) SEQUENCE DESCRIPTION: SEQ ID NO: 23:

Xaa Glu Xaa Asp Xaa Xaa Xaa Xaa Xaa Tyr
                 5                       10
```

( 2 ) INFORMATION FOR SEQ ID NO: 24:

```
    ( i ) SEQUENCE CHARACTERISTICS:
            ( A ) LENGTH: 10 amino acids
            ( B ) TYPE: amino acid
            ( D ) TOPOLOGY: linear ( i i ) MOLECULE TYPE: protein ( i x ) FEATURE:
            ( A ) NAME/KEY: HLA-B44 motif ( x i ) SEQUENCE DESCRIPTION: SEQ ID NO: 24:

Xaa Glu Xaa Val Xaa Xaa Xaa Xaa Xaa Tyr
                 5                       10
```

( 2 ) INFORMATION FOR SEQ ID NO: 25:

```
    ( i ) SEQUENCE CHARACTERISTICS:
            ( A ) LENGTH: 10 amino acids
            ( B ) TYPE: amino acid
            ( D ) TOPOLOGY: linear ( i i ) MOLECULE TYPE: protein ( i x ) FEATURE:
            ( A ) NAME/KEY: MAGE-1/HLA-B44

( x i ) SEQUENCE DESCRIPTION: SEQ ID NO: 25:

Lys Glu Ala Asp Pro Thr Gly His Ser Tyr
                 5                       10
```

( 2 ) INFORMATION FOR SEQ ID NO: 26:

```
    ( i ) SEQUENCE CHARACTERISTICS:
            ( A ) LENGTH: 10 amino acids
            ( B ) TYPE: amino acid
            ( D ) TOPOLOGY: linear ( i i ) MOLECULE TYPE: protein ( i x ) FEATURE:
            ( A ) NAME/KEY: Mage-2/HLA-B44

( x i ) SEQUENCE DESCRIPTION: SEQ ID NO: 26:

Val Glu Val Val Pro Ile Ser His Leu Tyr
                 5                       10
```

(2) INFORMATION FOR SEQ ID NO: 27:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: Mage-4/HLA-B44

(xi) SEQUENCE DESCRIPTION: SEQ ID NO: 27:

Lys Glu Val Asp Pro Ala Ser Asn Thr Tyr
            5                    10

(2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: Mage-5/HLA-B44

(xi) SEQUENCE DESCRIPTION: SEQ ID NO: 28:

Met Glu Ala Asp Pro Thr Ser Asn Thr Tyr
            5                    10

(2) INFORMATION FOR SEQ ID NO: 29:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: Mage-6/HLA-B44

(xi) SEQUENCE DESCRIPTION: SEQ ID NO: 29:

Met Glu Val Asp Pro Ile Gly His Val Tyr
            5                    10

(2) INFORMATION FOR SEQ ID NO: 30:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: Mage-12/HLA-B44

(xi) SEQUENCE DESCRIPTION: SEQ ID NO: 30:

Val Glu Val Val Arg Ile Gly His Leu Tyr
            5                    10